(12) United States Patent
Pericle et al.

(10) Patent No.: US 11,059,901 B2
(45) Date of Patent: Jul. 13, 2021

(54) COMPOSITIONS AND METHODS RELATED TO XCT ANTIBODIES

(71) Applicant: AGIL VAX, INC., Albuquerque, NM (US)

(72) Inventors: Federica Pericle, Albuquerque, NM (US); John O'Rourke, Albuquerque, NM (US); Federica Cavallo, Albuquerque, NM (US)

(73) Assignee: Agilvax Inc., Albuquerque, NM (US)

( * ) Notice: Subject to any disclaimer, the term of this patent is extended or adjusted under 35 U.S.C. 154(b) by 0 days.

(21) Appl. No.: 16/609,704

(22) PCT Filed: Apr. 30, 2018

(86) PCT No.: PCT/US2018/030276
§ 371 (c)(1),
(2) Date: Oct. 30, 2019

(87) PCT Pub. No.: WO2018/204278
PCT Pub. Date: Nov. 8, 2018

(65) Prior Publication Data
US 2020/0148784 A1    May 14, 2020

Related U.S. Application Data

(60) Provisional application No. 62/492,912, filed on May 1, 2017.

(51) Int. Cl.
*C07K 16/30* (2006.01)

(52) U.S. Cl.
CPC ...... *C07K 16/3015* (2013.01); *C07K 2317/24* (2013.01); *C07K 2317/622* (2013.01)

(58) Field of Classification Search
CPC ............ C07K 16/3015; C07K 2317/24; C07K 2317/622; C07K 16/18
See application file for complete search history.

(56) References Cited

U.S. PATENT DOCUMENTS

| 6,329,503 | B1 | 12/2001 | Afar et al. | |
|---|---|---|---|---|
| 2003/0224454 | A1* | 12/2003 | Ryseck | C07K 14/47 435/7.1 |
| 2007/0087006 | A1 | 4/2007 | Frantz et al. | |
| 2018/0360935 | A1* | 12/2018 | Cavallo | A61K 35/76 |

FOREIGN PATENT DOCUMENTS

WO    WO 2017/106806    6/2017

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Briggs et al., "Paracrine Induction of HIF by Glutamate in Breast Cancer: EgIN1 Senses Cysteine" *Cell* 2016, 166(1), 126-139.
Chen et al., "Disruption of xCT inhibits cancer cell metastasis via the caveolin-1/beta-catenin pathway" *Oncogene* 2009, 28(4), 599-609.
Guan et al., "The xc-cystine/glutamate antiporter as a potential therapeutic target for small-cell lung cancer: use of sulfasalazine" *Cancer Chemother Pharmacol.* 2009, 64(3), 463-472.
Guo et al., "Disruption of xCT inhibits cell growth via the ROS/autophagy pathway in hepatocellular carcinoma" *Cancer Lett.* 2011, 312(1), 55-61.
Hasegawa et al., "Functional interactions of the cystine/glutamate antiporter, CD44v and MUC1-C oncoprotein in triple-negative breast cancer cells" *Oncotarget* 2016, 7(11), 11756-11769.
International Search Report and Written Opinion issued in corresponding application No. PCT/US2018/030276, dated Jul. 31, 2018.
Ishimoto et al., "CD44 variant regulates redox status in cancer cells by stabilizing the xCT subunit of system xc(–) and thereby promotes tumor growth" *Cancer Cell* 2011, 19(3), 387-400.
Ju et al., "Redox Regulation of Stem-like Cells Though the CD44v-xCT Axis in Colorectal Cancer: Mechanisms and Therapeutic Implications" *Theranostics* 2016, 6(8), 1160-1175.
Lanzardo et al., "Immunotargeting of Antigen xCT Attenuates Stem-like Cell Behavior and Metastatic Progression in Breast Cancer" *Cancer Res.* 2016, 76(1), 62-72.
Nagano et al., "Redox regulation in stem-like cancer cells by CD44 variant isoforms" *Oncogene* 2013, 32(44), 5191-5198.
Robe et al., "Early termination of ISRCTN45828668, a phase 1/2 prospective, randomized study of sulfasalazine for the treatment of progressing malignant gliomas in adults" *BMC Cancer* 2009, 9(372), 1-8.
Shih et al., "xCT Cystine Transporter Expression in HEK293 Cells: Pharmacology and Localization" *Biochemical and Biophysical Research Communications* 2001, 282(5), 1132-1137.
Shitara et al., "Subgroup analyses of the safety and efficacy of ramucirumab in Japanese and Western patients in RAINBOW: a randomized clinical trial in second-line treatment of gastric cancer" *Gastric Cancer* 2016, 19, 927-938.
Timmerman et al., "Glutamine sensitivity analysis identifies the xCT antiporter as a common triple-negative breast tumor therapeutic target" *Cancer Cell* 2013, 24(4), 450-465.
Yoshikawa et al., "xCT inhibition depletes CD44v-expressing tumor cells that are resistant to EGFR-targeted therapy in head and neck squamous cell carcinoma" *Cancer Res.* 2013, 73(6), 1855-1866.

\* cited by examiner

*Primary Examiner* — Julie Wu
*Assistant Examiner* — Cheom-Gil Cheong

(57) ABSTRACT

Certain embodiments are directed to therapeutic compositions having an xCT specific antibody.

14 Claims, 14 Drawing Sheets
Specification includes a Sequence Listing.

SEQUENCE LISTING

<160> NUMBER OF SEQ ID NOS: 22

<210> SEQ ID NO 1
<211> LENGTH: 501
<212> TYPE: PRT
<213> ORGANISM: Homo sapiens

<400> SEQUENCE: 1

```
Met Val Arg Lys Pro Val Val Ser Thr Ile Ser Lys Gly Gly Tyr Leu
1               5                   10                  15

Gln Gly Asn Val Asn Gly Arg Leu Pro Ser Leu Gly Asn Lys Glu Pro
            20                  25                  30

Pro Gly Gln Glu Lys Val Gln Leu Lys Arg Lys Val Thr Leu Leu Arg
        35                  40                  45

Gly Val Ser Ile Ile Ile Gly Thr Ile Ile Gly Ala Gly Ile Phe Ile
    50                  55                  60

Ser Pro Lys Gly Val Leu Gln Asn Thr Gly Ser Val Gly Met Ser Leu
65                  70                  75                  80

Thr Ile Trp Thr Val Cys Gly Val Leu Ser Leu Phe Gly Ala Leu Ser
                85                  90                  95

Tyr Ala Glu Leu Gly Thr Thr Ile Lys Lys Ser Gly Gly His Tyr Thr
            100                 105                 110
```

```
Tyr Ile Leu Glu Val Phe Gly Pro Leu Pro Ala Phe Val Arg Val Trp
            115                 120                 125

Val Glu Leu Leu Ile Ile Arg Pro Ala Thr Ala Val Ile Ser Leu
130                 135                 140

Ala Phe Gly Arg Tyr Ile Leu Glu Pro Phe Phe Ile Gln Cys Glu Ile
145                 150                 155                 160

Pro Glu Leu Ala Ile Lys Leu Ile Thr Ala Val Gly Ile Thr Val Val
                165                 170                 175

Met Val Leu Asn Ser Met Ser Val Ser Trp Ser Ala Arg Ile Gln Ile
            180                 185                 190

Phe Leu Thr Phe Cys Lys Leu Thr Ala Ile Leu Ile Ile Val Pro
        195                 200                 205

Gly Val Met Gln Leu Ile Lys Gly Gln Thr Gln Asn Phe Lys Asp Ala
210                 215                 220

Phe Ser Gly Arg Asp Ser Ser Ile Thr Arg Leu Pro Leu Ala Phe Tyr
225                 230                 235                 240

Tyr Gly Met Tyr Ala Tyr Ala Gly Trp Phe Tyr Leu Asn Phe Val Thr
                245                 250                 255

Glu Glu Val Glu Asn Pro Glu Lys Thr Ile Pro Leu Ala Ile Cys Ile
            260                 265                 270

Ser Met Ala Ile Val Thr Ile Gly Tyr Val Leu Thr Asn Val Ala Tyr
        275                 280                 285

Phe Thr Thr Ile Asn Ala Glu Glu Leu Leu Leu Ser Asn Ala Val Ala
    290                 295                 300

Val Thr Phe Ser Glu Arg Leu Leu Gly Asn Phe Ser Leu Ala Val Pro
305                 310                 315                 320

Ile Phe Val Ala Leu Ser Cys Phe Gly Ser Met Asn Gly Gly Val Phe
                325                 330                 335

Ala Val Ser Arg Leu Phe Tyr Val Ala Ser Arg Glu Gly His Leu Pro
            340                 345                 350

Glu Ile Leu Ser Met Ile His Val Arg Lys His Thr Pro Leu Pro Ala
        355                 360                 365

Val Ile Val Leu His Pro Leu Thr Met Ile Met Leu Phe Ser Gly Asp
370                 375                 380

Leu Asp Ser Leu Leu Asn Phe Leu Ser Phe Ala Arg Trp Leu Phe Ile
385                 390                 395                 400

Gly Leu Ala Val Ala Gly Leu Ile Tyr Leu Arg Tyr Lys Cys Pro Asp
                405                 410                 415

Met His Arg Pro Phe Lys Val Pro Leu Phe Ile Pro Ala Leu Phe Ser
            420                 425                 430

Phe Thr Cys Leu Phe Met Val Ala Leu Ser Leu Tyr Ser Asp Pro Phe
        435                 440                 445

Ser Thr Gly Ile Gly Phe Val Ile Thr Leu Thr Gly Val Pro Ala Tyr
    450                 455                 460

Tyr Leu Phe Ile Ile Trp Asp Lys Lys Pro Arg Trp Phe Arg Ile Met
465                 470                 475                 480

Ser Glu Lys Ile Thr Arg Thr Leu Gln Ile Ile Leu Glu Val Val Pro
                485                 490                 495

Glu Glu Asp Lys Leu
            500

<210> SEQ ID NO 2
<211> LENGTH: 10
<212> TYPE: PRT
```

<213> ORGANISM: Artificial Sequence
<220> FEATURE:
<223> OTHER INFORMATION: Synthetic Peptide

<400> SEQUENCE: 2

Ser Pro Lys Gly Val Leu Gln Asn Thr Gly
1               5                   10

<210> SEQ ID NO 3
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 3

Arg Pro Ala Ala Thr Ala Val Ile Ser Leu Ala Phe Gly Arg Tyr Ile
1               5                   10                  15

Leu Glu Pro Phe Phe Ile Gln Cys
            20

<210> SEQ ID NO 4
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 4

Met Gln Leu Ile Lys Gly Gln Thr Gln Asn Phe Lys Asp Ala Phe Ser
1               5                   10                  15

Gly Arg Asp Ser Ser Ile Thr Arg
            20

<210> SEQ ID NO 5
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 5

Ala Tyr Phe Thr Thr Ile Asn Ala Glu Glu Leu Leu Leu Ser Asn Ala
1               5                   10                  15

Val Ala Val Thr Phe Ser Glu Arg Leu Leu Gly Asn Phe Ser Leu
            20                  25                  30

<210> SEQ ID NO 6
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 6

Tyr Ser Asp Pro Phe Ser
1               5

<210> SEQ ID NO 7
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 7

```
Ser Pro Lys Gly Val Leu Gln Asn Thr Gly Ser Val Gly Met Ser Leu
1               5                   10                  15

Thr Ile Trp Thr
            20
```

<210> SEQ ID NO 8
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 8

```
Ile Leu Glu Pro Phe Phe Ile Gln Cys Glu Ile Pro Glu Leu
1               5                   10
```

<210> SEQ ID NO 9
<211> LENGTH: 22
<212> TYPE: PRT
<213> ORGANISM: Artificial Sequence
<220> FEATURE:
<223> OTHER INFORMATION: Synthetic peptide

<400> SEQUENCE: 9

```
Lys Gly Gln Thr Gln Asn Phe Lys Asp Ala Phe Ser Gly Arg Asp Ser
1               5                   10                  15

Ser Ile Thr Arg Leu Pro
            20
```

<210> SEQ ID NO 10
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 10

```
Tyr Phe Thr Thr Ile Asn Ala Glu Glu Leu Leu Ser Asn Ala Val
1               5                   10                  15

Ala Val Thr Phe Ser Glu Arg Leu Leu Gly
            20                  25
```

<210> SEQ ID NO 11
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 11

```
Gly Asp Leu Asp Ser Leu Leu Asn
1               5
```

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

```
Leu Tyr Ser Asp Pro Phe Ser Thr
1               5
```

<210> SEQ ID NO 13
<211> LENGTH: 1788
<212> TYPE: DNA
<213> ORGANISM: Mus musculus

<400> SEQUENCE: 13

```
atggaatgga gctgggtctt tctcttcctc ctgtcagtaa ctgcaggtgt ccaatcccag      60
gttcaactgc agcagtctgg ggctgagctg gtgaggcctg gggcttcagt gaagctgtcc     120
tgcaaggctt tgggctacac atttactgac tatgaaatgc actgggtgaa gcagacacct     180
gtgcatggcc tggaatggat tggagctatt catccaggaa gtggtggtac tgcctacaat     240
cagaagttca gggcaaggc acactgact gcagacaaat cctccagcac agcctacatg      300
gagctcagca gcctgacatc tgaggactct gctgtctatt actgtacaag acccctctac     360
tataggtacc ttactacttt tgactactgg ggccaaggca ccactctcac agtctcctca     420
gagagtcagt ccttcccaaa tgtcttcccc ctcgtctcct gcgagagccc cctgtctgat     480
aagaatctgg tggccatggg ctgcctggcc cgggacttcc tgcccagcac catttccttc     540
acctggaact accagaacaa cactgaagtc atccaggta tcagaacctt cccaacactg      600
aggacagggg gcaagtacct agccacctcg caggtgttgc tgtctcccaa gagcatcctt     660
gaaggttcag atgaatacct ggtatgcaaa atccactacg gaggcaaaaa cagagatctg     720
catgtgccca ttccagctgt cgcagagatg aaccccaatg taaatgtgtt cgtcccacca     780
cgggatggct tctctggccc tgcaccacgc aagtctaaac tcatctgcga ggccacgaac     840
ttcactccaa aaccgatcac agtatcctgg ctaaaggatg ggaagctcgt ggaatctggc     900
ttcaccacag atccggtgac catcgagaac aaaggatcca ccccaaac ctacaaggtc      960
ataagcacac ttaccatctc tgaaatcgac tggctgaacc tgaatgtgta cacctgccgt    1020
gtggatcaca gggtctcac cttcttgaag aacgtgtcct ccacatgtgc tgccagtccc     1080
tccacagaca tcctaacctt caccatcccc cctccttg ccgacatctt cctcagcaag      1140
tccgctaacc tgacctgtct ggtctcaaac ctggcaacct atgaaaccct gaatatctcc    1200
tgggcttctc aaagtggtga accactgaaa accaaaatta aaatcatgga aagccatccc    1260
aatggcacct tcagtgctaa gggtgtggct agtgtttgtg tggaagactg gaataacagg    1320
aaggaatttg tgtgtactgt gactcacagg gatctgcctt caccacagaa gaaattcatc    1380
tcaaaaccca tgaggtgca aaacatcca cctgctgtgt acctgctgcc accagctcgt      1440
gagcaactga acctgaggga gtcagccaca gtcacctgcc tggtgaaggg cttctctcct    1500
gcagacatca gtgtgcagtg gcttcagaga gggcaactct tgcccaaga gaagtatgtg     1560
accagtgccc cgatgccaga gcctgggcc ccaggcttct actttaccca cagcatcctg    1620
actgtgacag aggaggaatg gaactccgga gagacctata cctgtgttgt aggccacgag     1680
gccctgccac acctggtgac cgagaggacc gtggacaagt ccactggtaa acccacactg    1740
tacaatgtct ccctgatcat gtctgacaca ggcggcacct gctattga                 1788
```

<210> SEQ ID NO 14
<211> LENGTH: 595
<212> TYPE: PRT
<213> ORGANISM: Mus musculus

<400> SEQUENCE: 14

```
Met Glu Trp Ser Trp Val Phe Leu Phe Leu Leu Ser Val Thr Ala Gly
1               5                   10                  15

Val Gln Ser Gln Val Gln Leu Gln Gln Ser Gly Ala Glu Leu Val Arg
```

```
                20                  25                  30
Pro Gly Ala Ser Val Lys Leu Ser Cys Lys Ala Leu Gly Tyr Thr Phe
            35                  40                  45
Thr Asp Tyr Glu Met His Trp Val Lys Gln Thr Pro Val His Gly Leu
 50                  55                  60
Glu Trp Ile Gly Ala Ile His Pro Gly Ser Gly Thr Ala Tyr Asn
 65                  70                  75                  80
Gln Lys Phe Lys Gly Lys Ala Thr Leu Thr Ala Asp Lys Ser Ser Ser
                85                  90                  95
Thr Ala Tyr Met Glu Leu Ser Ser Leu Thr Ser Glu Asp Ser Ala Val
            100                 105                 110
Tyr Tyr Cys Thr Arg Pro Leu Tyr Tyr Arg Tyr Pro Tyr Tyr Phe Asp
        115                 120                 125
Tyr Trp Gly Gln Gly Thr Thr Leu Thr Val Ser Glu Ser Gln Ser
    130                 135                 140
Phe Pro Asn Val Phe Pro Leu Val Ser Cys Glu Ser Pro Leu Ser Asp
145                 150                 155                 160
Lys Asn Leu Val Ala Met Gly Cys Leu Ala Arg Asp Phe Leu Pro Ser
                165                 170                 175
Thr Ile Ser Phe Thr Trp Asn Tyr Gln Asn Asn Thr Glu Val Ile Gln
            180                 185                 190
Gly Ile Arg Thr Phe Pro Thr Leu Arg Thr Gly Gly Lys Tyr Leu Ala
        195                 200                 205
Thr Ser Gln Val Leu Leu Ser Pro Lys Ser Ile Leu Glu Gly Ser Asp
    210                 215                 220
Glu Tyr Leu Val Cys Lys Ile His Tyr Gly Gly Lys Asn Arg Asp Leu
225                 230                 235                 240
His Val Pro Ile Pro Ala Val Ala Glu Met Asn Pro Asn Val Asn Val
                245                 250                 255
Phe Val Pro Pro Arg Asp Gly Phe Ser Gly Pro Ala Pro Arg Lys Ser
            260                 265                 270
Lys Leu Ile Cys Glu Ala Thr Asn Phe Thr Pro Lys Pro Ile Thr Val
        275                 280                 285
Ser Trp Leu Lys Asp Gly Lys Leu Val Glu Ser Gly Phe Thr Thr Asp
    290                 295                 300
Pro Val Thr Ile Glu Asn Lys Gly Ser Thr Pro Gln Thr Tyr Lys Val
305                 310                 315                 320
Ile Ser Thr Leu Thr Ile Ser Glu Ile Asp Trp Leu Asn Leu Asn Val
                325                 330                 335
Tyr Thr Cys Arg Val Asp His Arg Gly Leu Thr Phe Leu Lys Asn Val
            340                 345                 350
Ser Ser Thr Cys Ala Ala Ser Pro Ser Thr Asp Ile Leu Thr Phe Thr
        355                 360                 365
Ile Pro Pro Ser Phe Ala Asp Ile Phe Leu Ser Lys Ser Ala Asn Leu
    370                 375                 380
Thr Cys Leu Val Ser Asn Leu Ala Thr Tyr Glu Thr Leu Asn Ile Ser
385                 390                 395                 400
Trp Ala Ser Gln Ser Gly Glu Pro Leu Glu Thr Lys Ile Lys Ile Met
                405                 410                 415
Glu Ser His Pro Asn Gly Thr Phe Ser Ala Lys Gly Val Ala Ser Val
            420                 425                 430
Cys Val Glu Asp Trp Asn Asn Arg Lys Glu Phe Val Cys Thr Val Thr
        435                 440                 445
```

-continued

His Arg Asp Leu Pro Ser Pro Gln Lys Lys Phe Ile Ser Lys Pro Asn
        450                 455                 460

Glu Val His Lys His Pro Ala Val Tyr Leu Leu Pro Pro Ala Arg
465                 470                 475                 480

Glu Gln Leu Asn Leu Arg Glu Ser Ala Thr Val Thr Cys Leu Val Lys
                485                 490                 495

Gly Phe Ser Pro Ala Asp Ile Ser Val Gln Trp Leu Gln Arg Gly Gln
            500                 505                 510

Leu Leu Pro Gln Glu Lys Tyr Val Thr Ser Ala Pro Met Pro Glu Pro
        515                 520                 525

Gly Ala Pro Gly Phe Tyr Phe Thr His Ser Ile Leu Thr Val Thr Glu
    530                 535                 540

Glu Glu Trp Asn Ser Gly Glu Thr Tyr Thr Cys Val Val Gly His Glu
545                 550                 555                 560

Ala Leu Pro His Leu Val Thr Glu Arg Thr Val Asp Lys Ser Thr Gly
                565                 570                 575

Lys Pro Thr Leu Tyr Asn Val Ser Leu Ile Met Ser Asp Thr Gly Gly
            580                 585                 590

Thr Cys Tyr
        595

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 15

Asp Tyr Glu Met His
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 16

Ala Ile His Pro Gly Ser Gly Gly Thr Ala Tyr Asn Gln Lys Phe Lys
1               5                   10                  15

Gly

<210> SEQ ID NO 17
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 17

Pro Leu Tyr Tyr Arg Tyr Pro Tyr Tyr Phe Asp Tyr
1               5                   10

<210> SEQ ID NO 18
<211> LENGTH: 708
<212> TYPE: DNA
<213> ORGANISM: Mus musculus

<400> SEQUENCE: 18

```
atggatttc aggtgcagat tttcagcttc ctgctaatca gtgcctcagt cataatgtcc    60
agaggacaaa ttgttctcac ccagtctcca gcaatcatgt ctgcatctcc aggggagaag   120
gtcaccatat cctgcagtgc cagctcaagt gtaagttaca tgtactggta ccagcagaag   180
ccaggatcct cccccaaacc ctggatttat cgcacatcca acctggcttc tggagtccct   240
gctcgcttca gtggcagtgg gtctgggacc tcttactctc tcacaatcag cagcatggag   300
gctgaagatg ctgccactta ttactgccag cagtatcata gttacccgct cacgttcggt   360
gctgggacca agctggagct gaaacgggct gatgctgcac caactgtatc catcttccca   420
ccatccagtg agcagttaac atctggaggt gcctcagtcg tgtgcttctt gaacaacttc   480
taccccaaag acatcaatgt caagtggaag attgatggca gtgaacgaca aaatggcgtc   540
ctgaacagtt ggactgatca ggacagcaaa gacagcacct acagcatgag cagcaccctc   600
acgttgacca aggacgagta tgaacgacat aacagctata cctgtgaggc cactcacaag   660
acatcaactt cacccattgt caagagcttc aacaggaatg agtgttag               708
```

<210> SEQ ID NO 19
<211> LENGTH: 235
<212> TYPE: PRT
<213> ORGANISM: Mus musculus

<400> SEQUENCE: 19

```
Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Ser Cys Ser Ala Ser
        35                  40                  45

Ser Ser Val Ser Tyr Met Tyr Trp Tyr Gln Gln Lys Pro Gly Ser Ser
    50                  55                  60

Pro Lys Pro Trp Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Tyr
            100                 105                 110

His Ser Tyr Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

```
<210> SEQ ID NO 20
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 20

Ser Ala Ser Ser Ser Val Ser Tyr Met Tyr
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 21

Arg Thr Ser Asn Leu Ala Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 22

Gln Gln Tyr His Ser Tyr Pro Leu Thr
1               5
```

COMPOSITIONS AND METHODS RELATED TO XCT ANTIBODIES

CROSS REFERENCE TO RELATED APPLICATIONS

This application is a national phase under 35 U.S.C. § 371 of International Application No. PCT/US2018/030276, filed Apr. 30, 2018, which claims the benefit of priority of U.S. Provisional Patent Application No. 62/492,912, filed May 1, 2017, the entire contents of each of which are hereby incorporated by reference in their entirety.

BACKGROUND

Triple negative breast cancer (TNBC) is an aggressive form of breast cancer that lacks the estrogen, progesterone and HER2 receptors, and accounts for 15-20% of all breast cancers in the US. TNBC has higher rates of relapse and poorer outcomes than other forms of breast cancer and owing to the lack of targetable surface receptors, TNBC are resistant to hormonal and HER2-targeted therapies. The particularly aggressive features of TNBC may be due to the enrichment of cancer stem cells (CSC) that have the unique biological properties necessary for maintenance and spreading of the tumor and through asymmetric division, can differentiate into cancer cells that compose the tumor bulk (Magee et al., Cancer Cell 2012, 21(3):283-96). Due to their resistance to traditional radio- and chemotherapies (Nagano et al., Oncogene 2013, 32(44):5191-8), CSC represent a reservoir for the relapse, metastatic evolution, and progression of the disease after treatment. Therefore, successful eradication of CSC represents a major barrier towards effective cancer treatments.

The ability of CSC to resist common cytotoxic therapies relies on different mechanisms, including improved detoxification ability. The cystine-glutamate antiporter protein xCT (SLC7A11) regulates cysteine intake, conversion to cysteine and subsequent glutathione synthesis, protecting cells against oxidative and chemical insults via the p38$^{MAPK}$ pathway (Chen et al., Oncogene 2009, 28(4):599-609; Guo et al., Cancer Lett. 2011, 312(1):55-61). xCT expression is highly restricted to a few normal cell types (neurons and a subset of macrophages) but elevated levels of xCT protein are observed in a high percentage of invasive mammary ductal tumors including TNBC (Lanzardo et al. Cancer Res. 2016, 76(1):62-72). High levels of xCT mRNA and protein correlate with significant reduction in distal metastases-free and overall survival (Briggs et al., Cell 2016, 166(1):126-39; Gyorffy et al., Breast Cancer Res Treat. 2010, 123(3):725-31). xCT expression is upregulated in breast CSC (BCSC) and other solid tumor stem cells, and several studies show that xCT physically interacts with the well-known stem cell marker, CD44 (Nagano et al., Oncogene 2013, 32(44):5191-8; Hasegawa et al., Oncotarget 2016, 7(11):11756-69; Ishimoto et al., Cancer Cell 2011, 19(3):387-400; Ju et al., Mechanisms and Therapeutic Implications. Theranostics 2016, 6(8):1160-75; Yoshikawa et al., Cancer Res. 2013, 73(6):1855-66). The frequency of xCT expression on a variety of CSC suggests that therapies targeting xCT may be effective for a variety of tumors with high stem cell frequencies including gastrointestinal and pancreatic cancers.

A direct role for xCT in breast cancer metastasis was shown by inhibiting xCT function with the small molecule sulfasalazine (SASP), which resulted in significant decreases in metastatic foci in animal models and reductions in the frequency of CSC (Nagano et al., Oncogene 2013, 32(44):5191-8; Chen et al., Oncogene 2009, 28(4):599-609; Guan et al., Cancer Chemother Pharmacol. 2009, 64(3):463-72; Timmerman et al., Cancer Cell 2013, 24(4):450-65). However, SASP is labile and insoluble under physiological conditions, has vast off-target effects, low bioavailability and requires high doses to inhibit xCT in vivo (Timmerman et al., Cancer Cell 2013, 24(4):450-65; shitara et al., Gastric Cancer 2016; Linares et al., Expert Opin Drug Saf. 2011, 10(2):253-63; Robe et al., BMC Cancer 2009, 9:372). Therefore, new therapeutic modalities specifically targeting xCT need to be developed for clinical use.

SUMMARY

Certain embodiments are directed to therapeutic antibodies and monoclonal antibodies that specifically bind xCT epitopes. Certain aspects are directed to monoclonal antibodies (MABs) against xCT peptides and/or epitopes including, but not limited to peptides or epitopes present in extracellular domain (ECD) 1, 2, 3, 4, 6, or various combinations thereof. In certain instances the MABs can be produced using VLP-based vaccination. Such VLPs displaying the various xCT peptides can be used to induce an epitope specfici immune response that can be used to produce MABs.

In certain aspects the peptides or epitopes are defined as SPKGVLQNTG (SEQ ID NO:2), RPAATAVISLAFGRYILEPFFIQC (SEQ ID NO:3), MQLIKGQTQNFKDAFSGRDSSITR (SEQ ID NO:4), AYFTTINAEELLLSNAVAVTFSERLLGNFSL (SEQ ID NO:5), YSDPFS (SEQ ID NO:6), SPKGVLQNTGSVGMSLTIWT (SEQ ID NO:7), ILEPFFIQCEIPEL (SEQ ID NO:8), KGQTQNFKDAFSGRDSSITRLP (SEQ ID NO:9), YFTTINAEELLLSNAVAVTFSERLLG (SEQ ID NO:10), GDLDSLLN (SEQ ID NO:11), and LYSDPFST (SEQ ID NO:12). Other embodiments are directed to an antibody that specifically binds a peptide having 3, 4, 5, 6, 7, 8, 9, 10, 11, 12, or more consecutive amino acids of SEQ ID NO:2, 3, 4, 5, 6, 7, 8, 9, 10, 11, or 12.

The present invention provides high affinity antibodies and antibody fragments that specifically bind xCT or an ECD of xCT. As used herein, the term antibody refers to a full length, complete antibody molecule as recognized in the art. The term fragment in the context of the present application refers to a portion of an antibody that retains the capability to bind to xCT, an xCT peptide, or an xCT epitope with high affinity and specificity. Antibody fragments can be defined based on how many domains are included and/or excluded from the original full domain structure. Hence, a fragment can mean Variable heavy (VH) or Variable light (VL) or Single chain Fv (VH-VL) or Fab (VL-CL-VH-CH1) or Fab2 (VL-CL-VH-CH1)2 or any of the above linked to anticancer moieties (e.g., chemotherapies or radiotherapies), small molecules, PEG, other protein domain(s), or labeling agents. A preferred example of such a fragment is a single chain antibody variable region fragment (ScFv). The term antibody, as used in this application, generally refers to complete antibody molecules or fragments, unless there is a statement to the contrary. Other xCT binding moieties can be engineered using the amino acid sequence of the complementary determining regions (CDRs) presented on an antibody or non-antibody framework or scaffold.

Antibodies are preferably human, humanized, chimeric, or ScFv antibodies or fragments. The antibodies and fragments of this invention are further provided as a pharmaceutical preparation for therapeutic use. The invention further provides recombinant DNA molecules encoding xCT antibodies of the invention and expression systems for producing or manufacturing the antibodies recombinantly.

The xCT binding agents (e.g., anti-xCT antibodies) of this invention are useful for treating conditions in which xCT is over-expressed, such as cancer. The antibodies can act through a specific high affinity interaction at the cell surface to induce apoptosis and cell kill by antibody dependent cellular cytotoxicity (ADCC) and complement dependent cytotoxicity (CDC).

Certain embodiments are directed to an xCT antibody that specifically binds an epitope defined by the amino acid sequence of SEQ ID NO:1, 2, 3, 4, 5, 6, 7, 8, 9, 10, 11, or 12, in certain aspects SEQ ID NO:4. In certain aspects the xCT antibody has a heavy chain comprising a CDR1 having the amino acid sequence of SEQ ID NO:15, a CDR2 having the amino acid sequence of SEQ ID NO:16, and a CDR3 having the amino acid sequence of SEQ ID NO:17. In another aspect the xCT antibody comprises a light chain comprising a CDR1 having the amino acid sequence of SEQ ID NO:20, a CDR2 having the amino acid sequence of SEQ ID NO:21, and a CDR3 having the amino acid sequence of SEQ ID NO:22. The antibody can comprise a heavy chain comprising a CDR1 having the amino acid sequence of SEQ ID NO:15, a CDR2 having the amino acid sequence of SEQ ID NO:16, and a CDR3 having the amino acid sequence of SEQ ID NO:17; and a light chain comprising a CDR1 having the amino acid sequence of SEQ ID NO:20, a CDR2 having the amino acid sequence of SEQ ID NO:21, and a CDR3 having the amino acid sequence of SEQ ID NO:22. In certain aspects the antibody or antibody fragment is human or humanized. In other aspects the antibody or antibody fragment thereof is a chimeric. The antibody can be an antibody fragment. In certain aspects the antibody fragment is an ScFv. The ScFv can be murine, human, or humanized.

This invention provides a therapeutic method of administering an effective amount of anti-xCT antibodies to a patient that suffers from a disease in which xCT is overexpressed, such as cancer. Cancers in which xCT is overexpressed include gastrointestinal cancers, including colorectal, pancreatic, stomach and others; lung cancer; breast cancer; leukemias, including acute myeloid leukemias; female reproductive cancers such as cervical, uterine and ovarian cancers; other epithelial cancers such as brain, prostate, liver, and kidney cancers. Particular aspects of the invention are directed to anti-xCT monoclonal antibody that can promote cancer cell apoptosis and may be used for therapeutic indications.

The present invention provides for a method of treating cancer comprising administering an effective amount of an anti-xCT antibody or antibody fragment to a patient in need thereof.

In one embodiment, the antibody or antibody fragment is humanized. In a particular embodiment the antibody is a monoclonal antibody or antibody fragment. In another embodiment, the antibody or antibody fragment is chimeric. In another embodiment, the antibody or antibody fragment is an ScFv. In another embodiment, the ScFv is human, murine, or humanized.

In one embodiment, the cancer is at least one selected from the group consisting of gastrointestinal cancer, lung cancer, breast cancer, leukemias, cervical cancer, uterine cancer, ovarian cancers, brain cancer, prostate cancer, liver cancer, and kidney cancer. In another embodiment, the patient is a human or a non-human animal. In another embodiment, the antibody or antibody fragment is administered parenterally, intraperitoneally intravenously or subcutaneous, orally, nasally, via inhalation or rectally. In another embodiment, the antibody or antibody fragment is administered intravenously at a dosage of from 5 mg/m$^2$ to 2000 mg/m$^2$.

The present invention also provides a method of inducing apoptosis in cells expressing xCT comprising contacting the cells with an effective amount of an anti-xCT antibody or antibody fragment. In certain aspects the targeted cells are cancer cells.

The present invention also provides a humanized murine anti-xCT antibody or antibody fragment. In a preferred embodiment, the antibody or antibody fragment contains the CDRs of monoclonal antibody that specifically bind the epitopes described herein. In another embodiment, the antibody or antibody fragment is modified with PEG. The present invention also provides an anti-xCT ScFv. In a preferred embodiment, the ScFv contains the CDRs of a monoclonal antibody that specifically bind the epitopes described herein. In another embodiment, the ScFv is modified with PEG. The present invention also provides a fragment of an anti-xCT antibody which has high affinity for xCT. In a preferred embodiment, the fragment contains the CDRs of monoclonal antibody that specifically bind the epitopes described herein. In another embodiment, the fragment is modified with PEG.

The present invention also provides a conjugate in which the antibody or fragment described above is conjugated to at least one other moiety. In certain aspects the moiety is a chemotherapy, a radiotherapy, or a detectable label.

The present invention also provides a pharmaceutical composition, comprising the antibody or fragment as discussed above and at least one pharmaceutical excipient. In one embodiment of the invention, the excipient is one or more of water, pH buffers, wetting agents, salts, reducing agents, sugars, glycerol, glycol, oils, preservatives and antimicrobials.

Certain embodiments are directed to a therapeutic antibody that binds an xCT peptide or epitope. In certain aspects VLPs or plasmids are produced that display or encode one or more xCT peptide or epitope. The full length xCT protein can have an amino acid sequence that is 98% to 100% identical to the amino acid sequence MVRKPVVSTISKG-GYLQGNVN-GRLPSLGNKEPPGQEKVQLKRKVTLLRGVSIIIGTII GAGIFIS-PKGVLQNTGSVGMSLTIWTVCGVLSLFGALSYAEL-GTTIKKSGGHYTYILE VFGPLPAFVRVWVELLIIR-PAATAVISLAFGRYILEPFFIQCEIPELAIKWAVGITVVM VLNSMSVSWSARIQIFLTFCKLTAILIIIVPGVMQ-LIKGQTQNFKDAFSGRDSSITRLPL AFYYGMYAY-AGWFYLNFVTEEVENPEKTIPLAICISMAIVTI-GYVLTNVAYFTTINAE ELLLSNAVAVTFSER-LLGNFSLAVPIFVALSCFGSMNGGVFAVSRLFYVAS-REGHLPE ILSMIHVRKHTPLPAVIVLHPLTMIMLF-SGDLDSLLNFLSFARWLFIGLAVAGLIYLRY KCPDMHRPFKVPLFIPALFSFTCLFMVALSLYSDPFST-GIGFVITLTGVPAYYLFIIWDK KPRWFRIM-SEKITRTLQIILEVVPEEDKL (SEQ ID NO:1). xCT peptides can be any or nucleic acids encode any 5, 6, 7, 8, 9, 10, 11, 12, 13, 14, 15, 16, 17, 18, 19, 20, 21, 22, 23, 24, 25, 26, 27, 28, 29, or 30 consecutive amino acid segment SEQ ID NO:1. In other embodiments the xCT protein can have a variant amino acid in that the xCT protein can be 85, 90, 95, or 98% identical to the amino acid sequence provided in SEQ ID NO:1. In other aspects the xCT protein can comprise 20, 30, 40, 50, 60, 70, 80, 90, 100, 150, 200, 250, 300, 350, 400, 450, 500, or 501 consecutive amino acids of SEQ ID NO:1, including all values and ranges there between, or a peptide of the same length having 85, 90, 95, 98, or 99% identity to SEQ ID NO:1.

In certain aspect an immunogenic peptide can be displayed or encoded by a virus like particle (VLP) using RNA bacteriophage coat proteins displaying heterologous peptides. VLPs expression plasmids are constructed to display the extracellular domains (ECD) or other peptides or epitopes of human xCT. In certain aspects ECDs or other xCT peptides can be displayed on the surface of VLPs using genetic insertion and/or chemical conjugation methods. In certain aspects the amino acid sequences of human xCT ECDs are ECD 1 corresponding to amino acids 65-74 of SEQ ID NO:1; ECD 2 corresponding to amino acids 135-158 of SEQ ID NO:1; ECD 3 corresponding to amino acids 211-234 of SEQ ID NO:1; ECD 4 corresponding to amino acids 287-317 of SEQ ID NO:1; and ECD 6 corresponding to amino acids 444-449 of SEQ ID NO:1.

In certain aspects the VLP is a MS2, Qβ (Q-beta), PP7 or AP205 VLP. The different xCT ECDs can be codon optimized for expression in *E. coli* and ligated into the amino terminus (N-terminus), carboxy terminus (C-terminus), or the AB loop of a RNA bacteriophage single-chain dimer coat protein.

In certain aspects the VLP is a Woodchuck Hepadnavirus Core-based VLP. The woodchuck hepadnavirus core-based virus-like particle (WHcAg-VLP) is used to display the xCT peptide. The WHcAG-VLP can display 270 copies of the xCT peptide per VLP in a loop conformation at one of three different display points. Codon optimized sequences of the various xCT peptides as described herein are generically inserted into the Woodchuck Hepadnavirus Core protein. In certain aspects the VLPs will be produced in *E. coli*.

The therapeutic compositions are administered in a manner compatible with the dosage formulation, and in such amount as will be prophylactically and/or therapeutically effective. The quantity to be administered depends on the subject to be treated. Precise amounts of active ingredient required to be administered depend on the judgment of the practitioner. The compositions may be given in a single dose schedule or preferably in a multiple-dose schedule. A multiple-dose schedule is one in which a primary course of administration may be with 1-10 separate doses, followed by other doses given at subsequent time intervals required to maintain and/or reinforce a therapeutic response, for example, at 1-4 months for a second dose and if needed, a subsequent dose(s) after several months.

Administration can be performed, for example, intravenously, orally, nasally, via implant, transmucosally, transdermally, intramuscularly, rectally, and subcutaneously. The following delivery systems, which employ a number of routinely used pharmaceutical carriers, are only representative of the many embodiments envisioned for administering the compositions of the invention. The manner of application may vary. Any of the conventional methods for administration of a polypeptide therapy are applicable. These are believed to include parenterally by injection and the like. The dosage of the composition will depend on the route of administration and will vary according to the size and health of the subject.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e., reduce tumor burden); lessen or reduce the number of cancerous cells in the body; prevent recurrence of cancer after surgical removal or other anti-cancer therapies; or ameliorate or alleviate the symptoms of the disease caused by the cancer.

The terms "inhibiting," "reducing," or "prevention," or any variation of these terms, when used in the claims or the specification includes any measurable decrease or complete inhibition to achieve a desired result.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(A) To analyze BCSC self-renewal, the number of secondary tumorspheres that formed in 3D culture were counted and plotted as number of spheres/10³ cells plated. (B) BCSC proliferation was assessed with acquired sphere images and measurement of mean sphere diameter was calculated using ImageJ software. (C) The ability of AX09 immune sera to inhibit xCT function was evaluated by measuring intercellular ROS levels. Dissociated spheres were incubated with 2,7 dihydrodichlorofluorescein diacetate and the ROS levels were evaluated by FACS. (D) To determine the frequency of BCSC in the tumorspheres, spheres were dissociated into single cell suspensions and analyzed for aldehyde dehydrogenase activity by incubating cells with ALDEFLUOR and analyzing cells by FACS. The percentage of ALDH positive cells (indicative of cancer stem/progenitor cells) were plotted.

Figure 2:
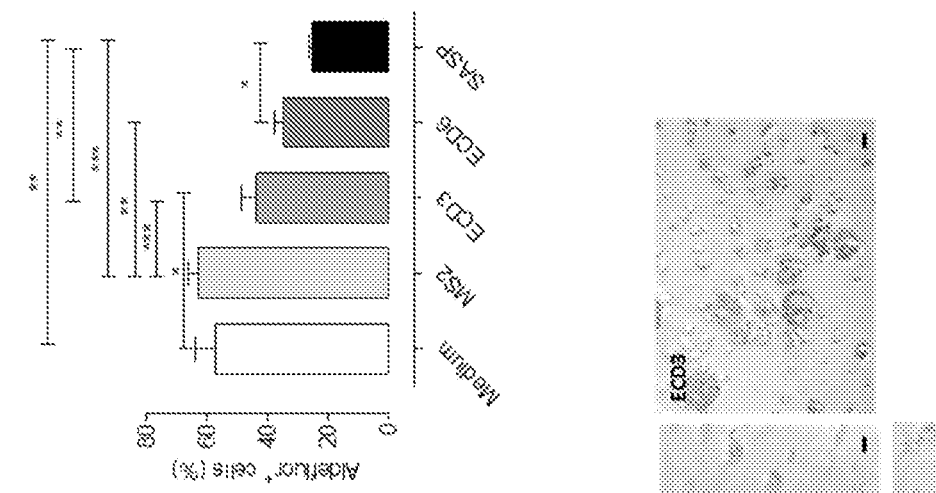
Figure 2:
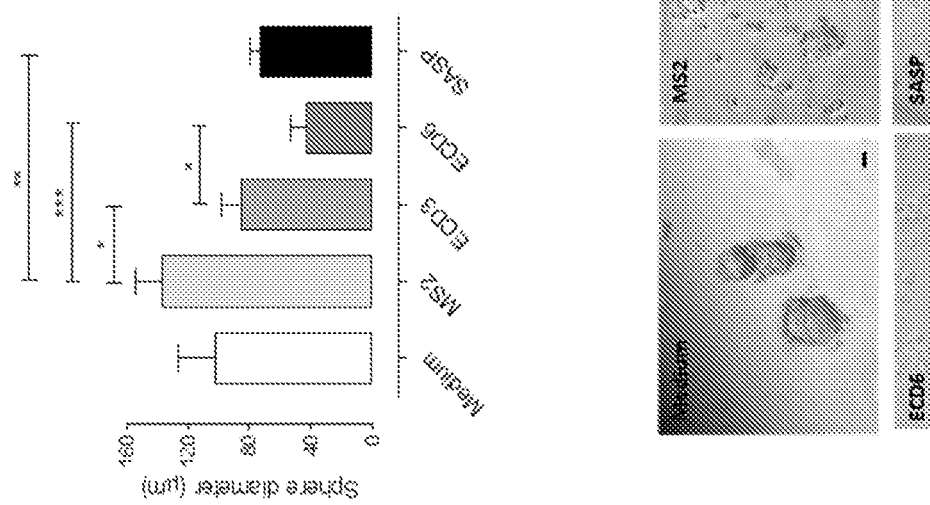
Figure 2:
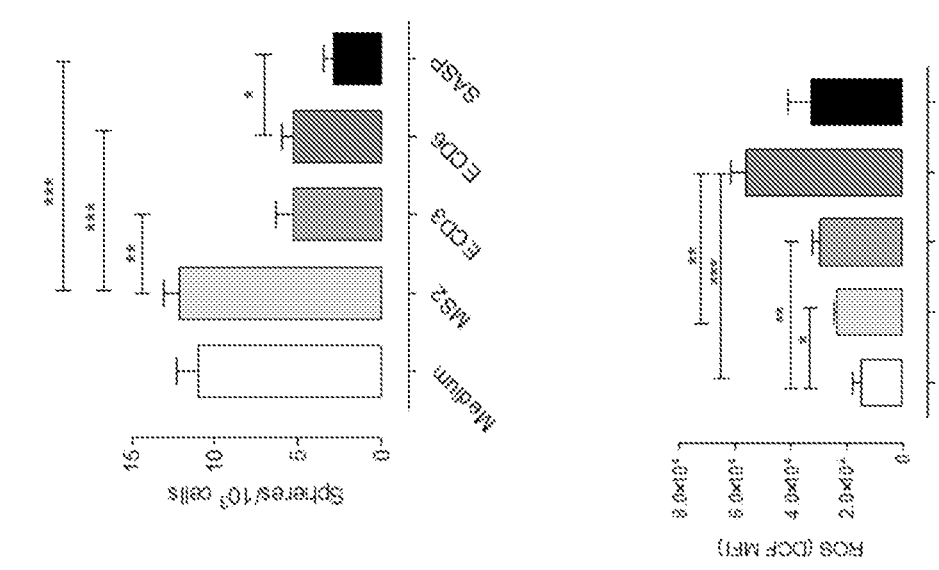
Figure 2:
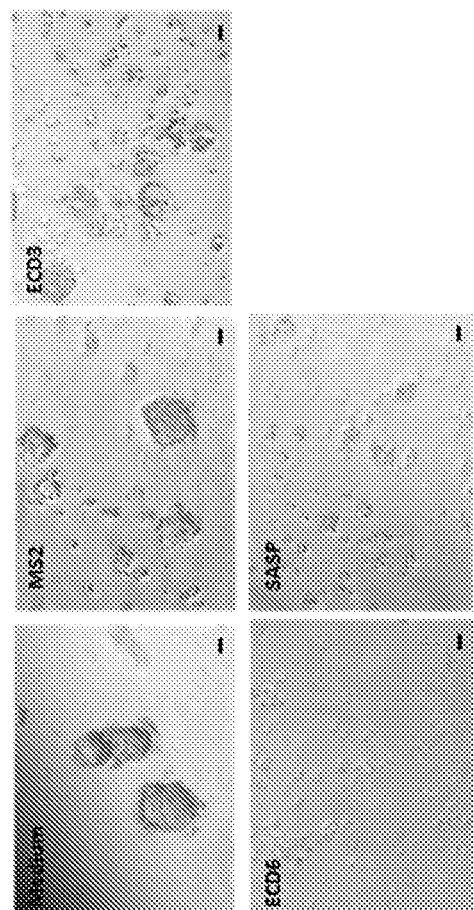

FIG. 2 Purified IgG incubated with triple negative breast cancer derived stem cells. Mouse TUBO derived cancer stem cells with both IgG purified from ECD6 and ECD3 VLPs.

Figure 3:
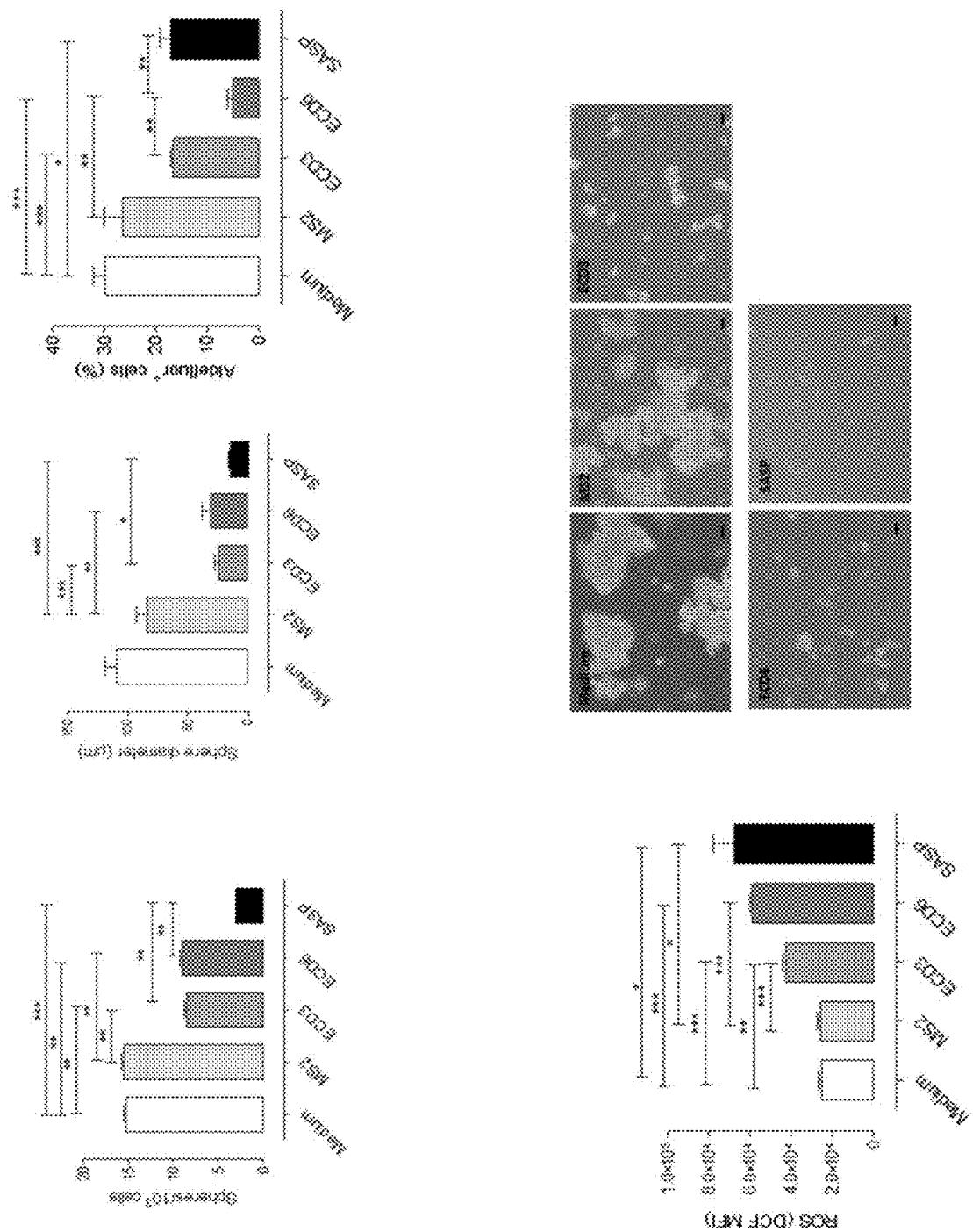

FIG. 3 Purified IgG incubated with triple negative breast cancer derived stem cells. Mouse 4T1 derived cancer stem cells with both IgG purified from ECD6 and ECD3 VLPs.

Figure 4:
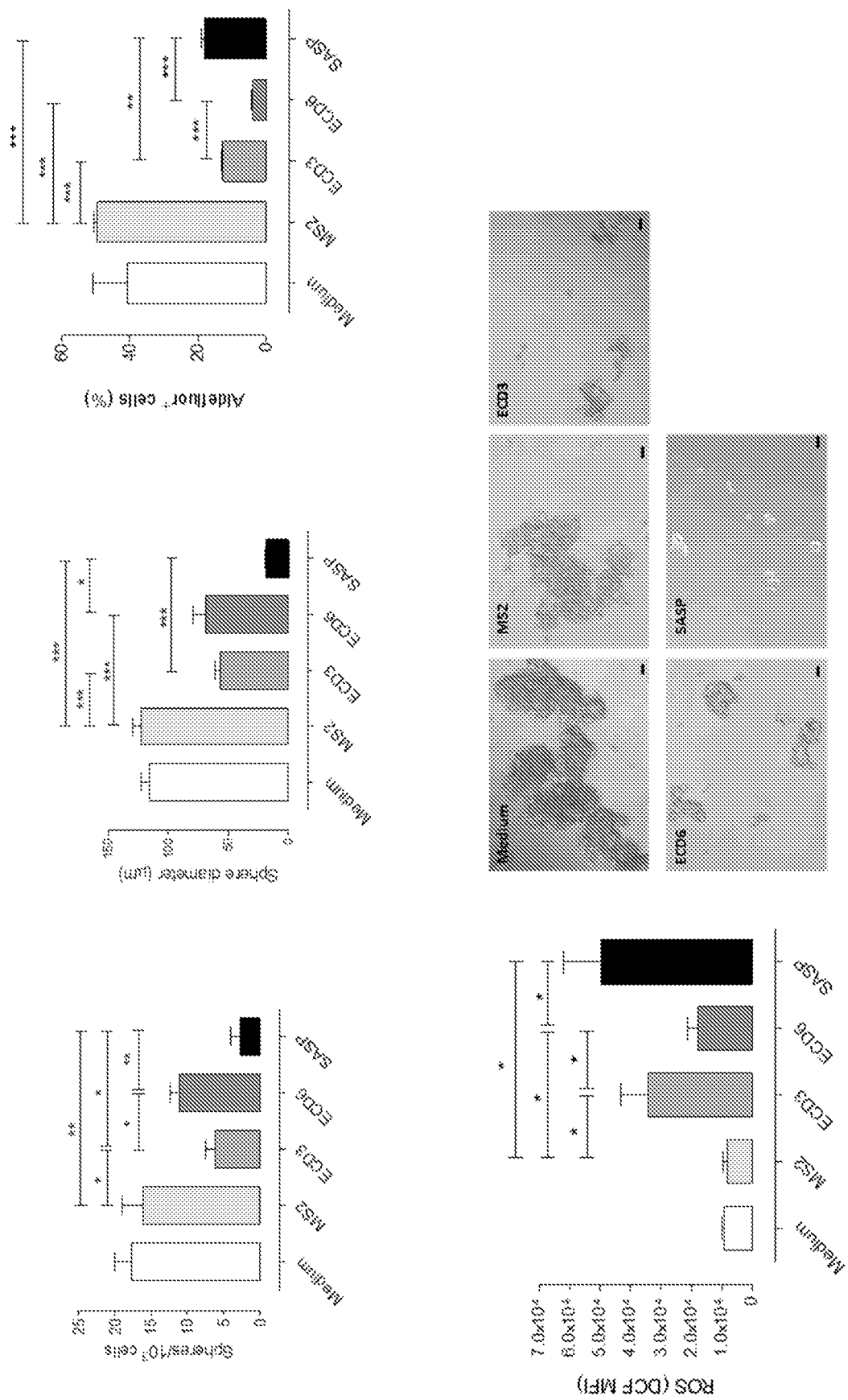

FIG. 4 Purified IgG incubated with triple negative breast cancer derived stem cells. Human HTC1806 derived cancer stem cells with both IgG purified from ECD6 and ECD3 VLPs.

Figure 5:
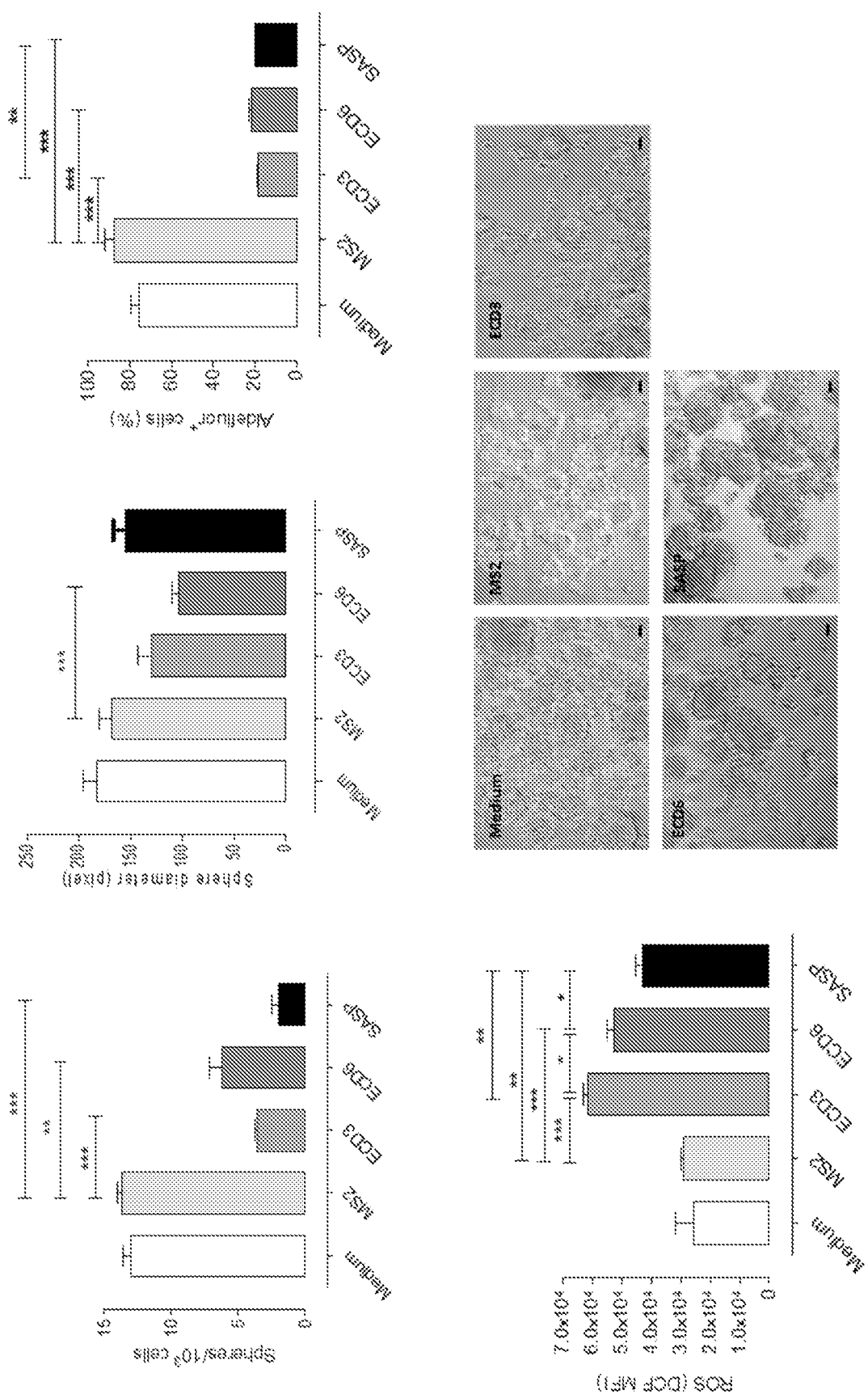

FIG. 5 Purified IgG incubated with triple negative breast cancer derived stem cells. Human MB-MDA 231 derived cancer stem cells with both IgG purified from ECD6 and ECD3 VLPs.

Figure 6:
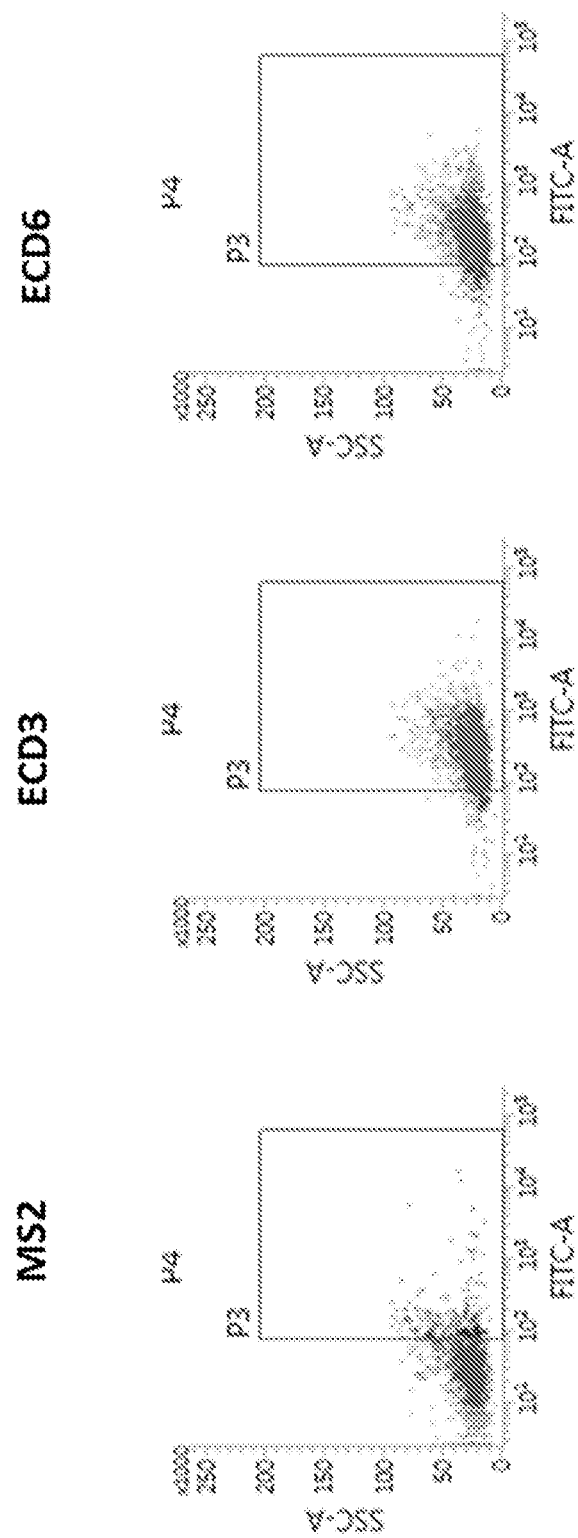

FIG. 6 FACS analysis from sera from vaccination protocols for elicited antibodies that bind to the extracellular regions of xCT from 4T1 cells, purified IgG shown.

Figure 1:
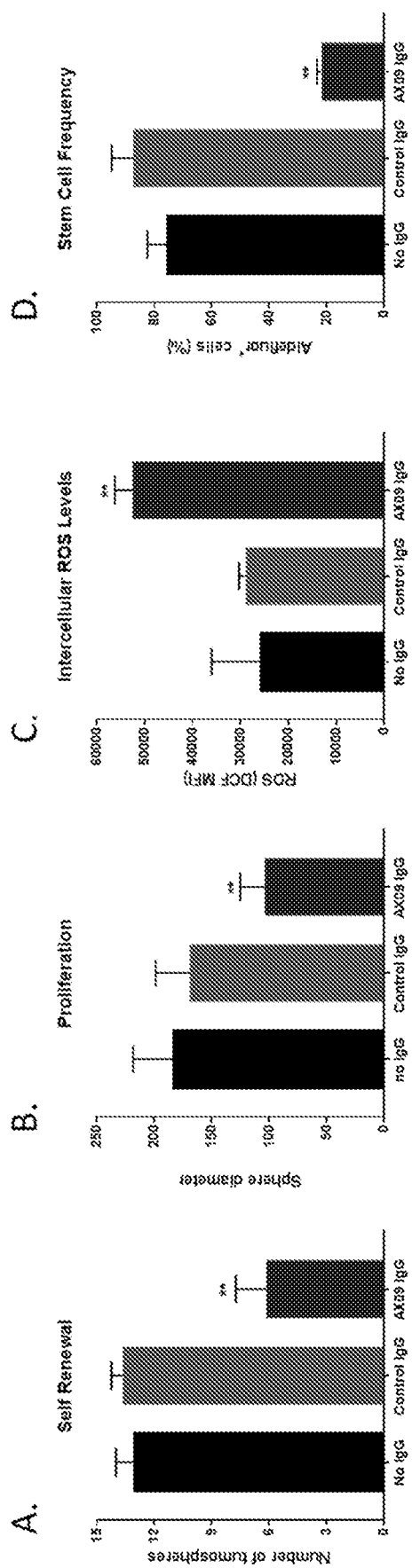
FIG. 1. AX09-induced antibodies affect BCSC biology and inhibit xCT function in human cells. Passage 1 MDA-MB-231 derived tumorspheres were dissociated and replated ($4*10^5$/well) with purified IgG isolated from control VLP or AX09 treated mice at 50 μg/ml in sphere medium. Media containing no IgG was used as a control. Cultures were analyzed five days later and each assay was done in triplicate. Error bars represent standard deviation and ** represents a p-value from student's t-test of <0.01.
Figure 7:
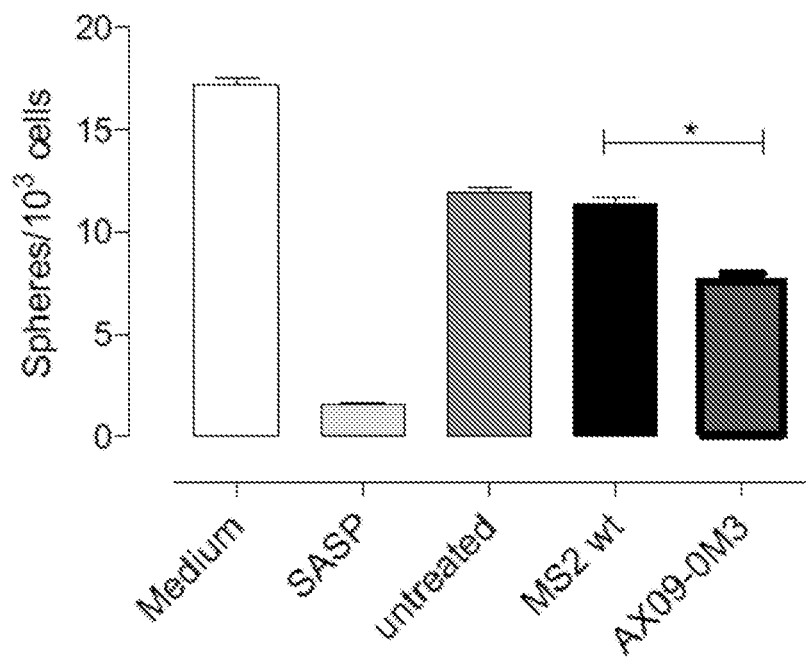

FIG. 7 4T1-derived tumorspheres were incubated for 5 days with medium, SASP (50 µM), or a 1:50 dilution of sera from vaccinated or untreated mice, to measure the sphere generating ability reported as tumorsphere number/10³ plated cells.

Figure 8:
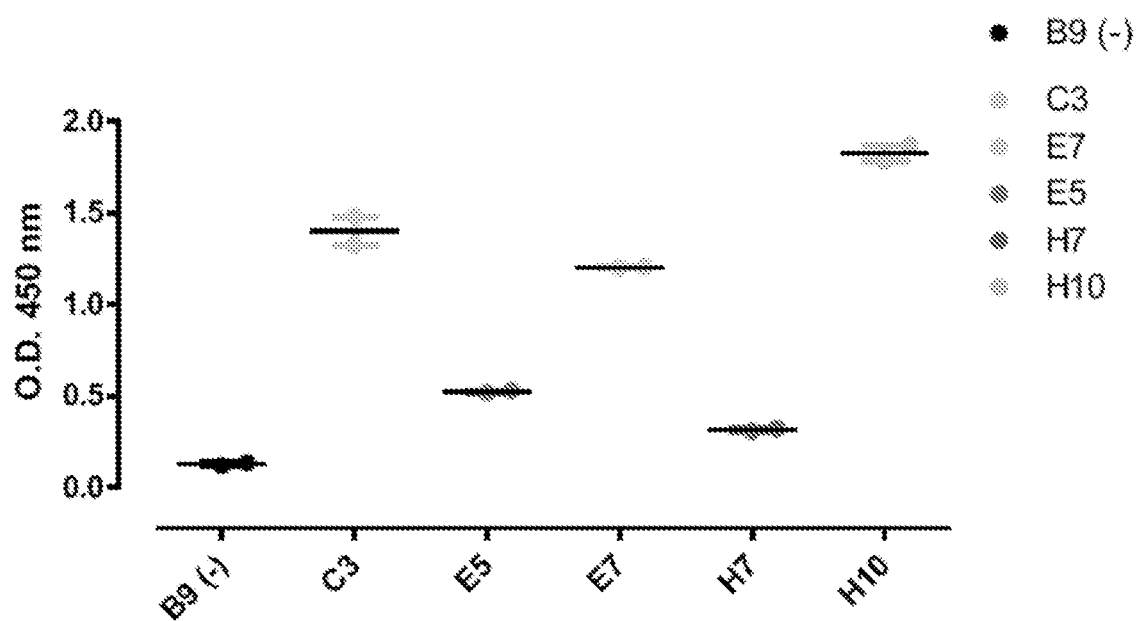

FIG. 8 Five clones were positive in ELISA against the mECD3 peptide, namely: 11D1/C3; 11D1/H7; 11D1/E7; 11D1/E5; 11D1/H10 in ELISA assays performed using the human-xCT protein.

Figure 9:
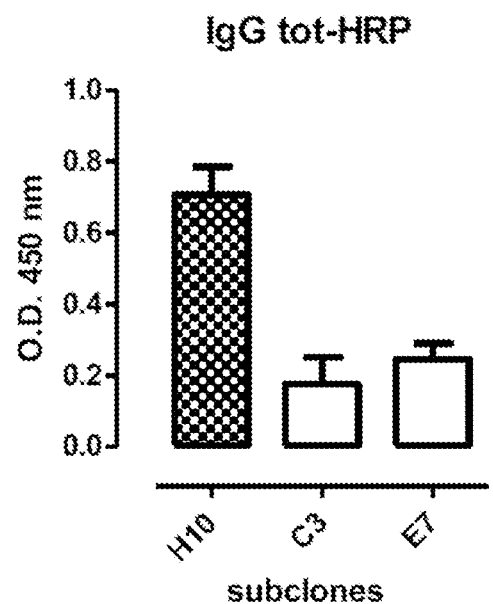

FIG. 9 Subclones: H10-C3-E7, were tested by ELISA against the human-xCT ECD3 peptide [1 µg/mL].

Figure 10:
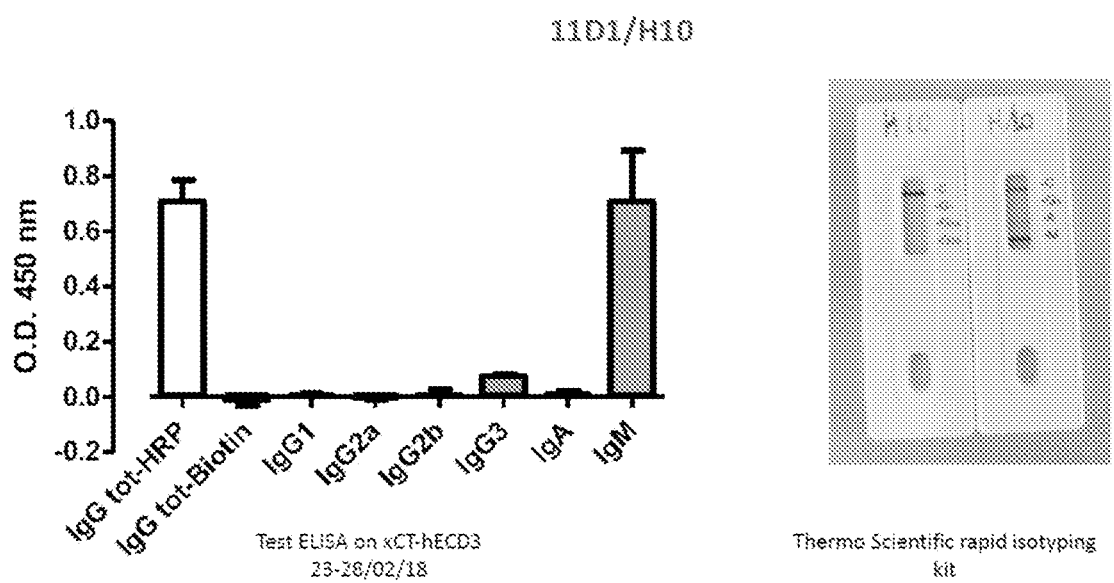

FIG. 10 From this ELISA H10 (from here called 11D1/H10) was chosen as a representative subclone producing anti-xCT Ig. In order to discriminate which Ig isotype was present into the supernatants from 11D1/H10, a Pierce rapid isotyping kit was used (#26178; Thermo Scientific).

Figure 11:
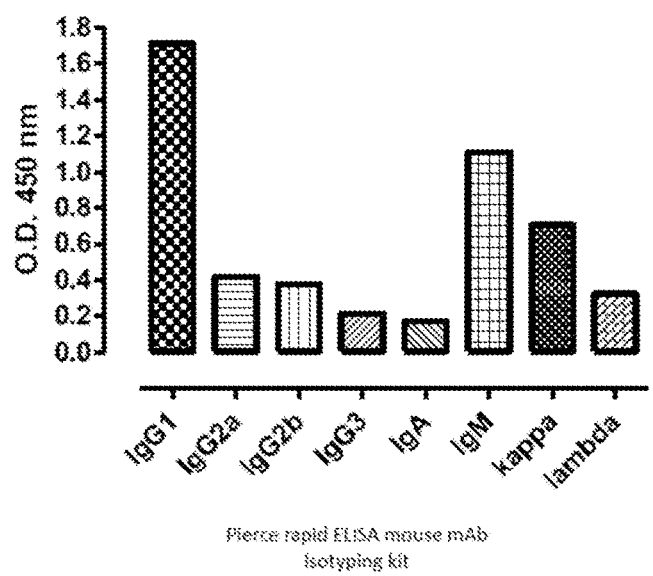
Figure 11:
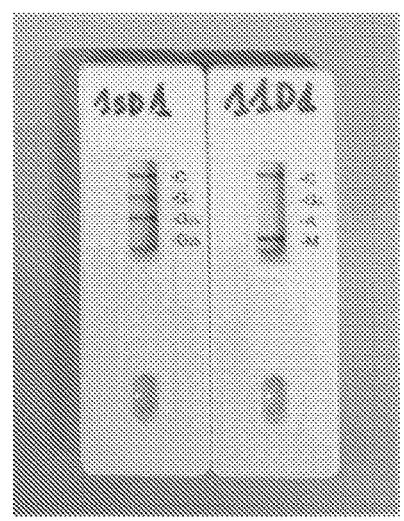
Figure 12:
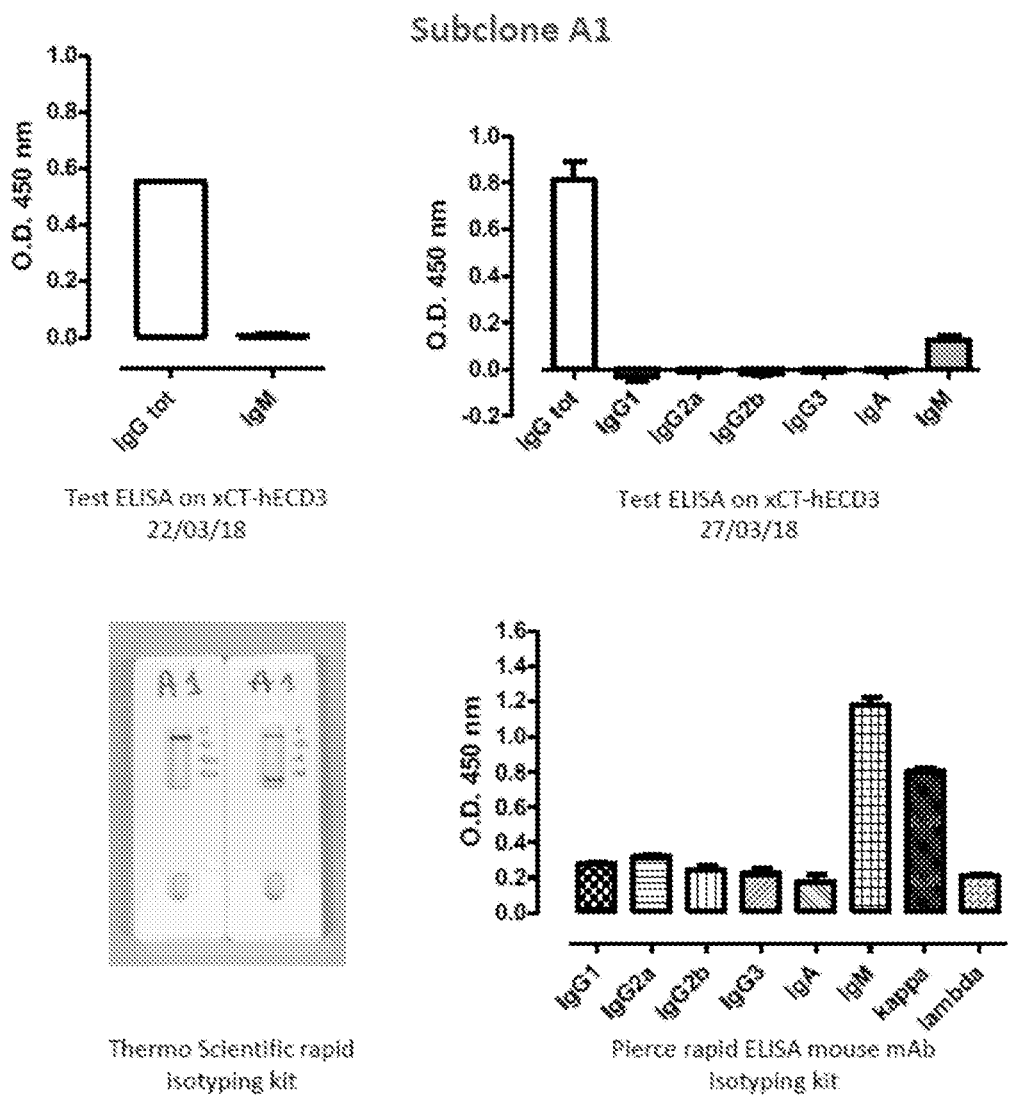
Figure 13:
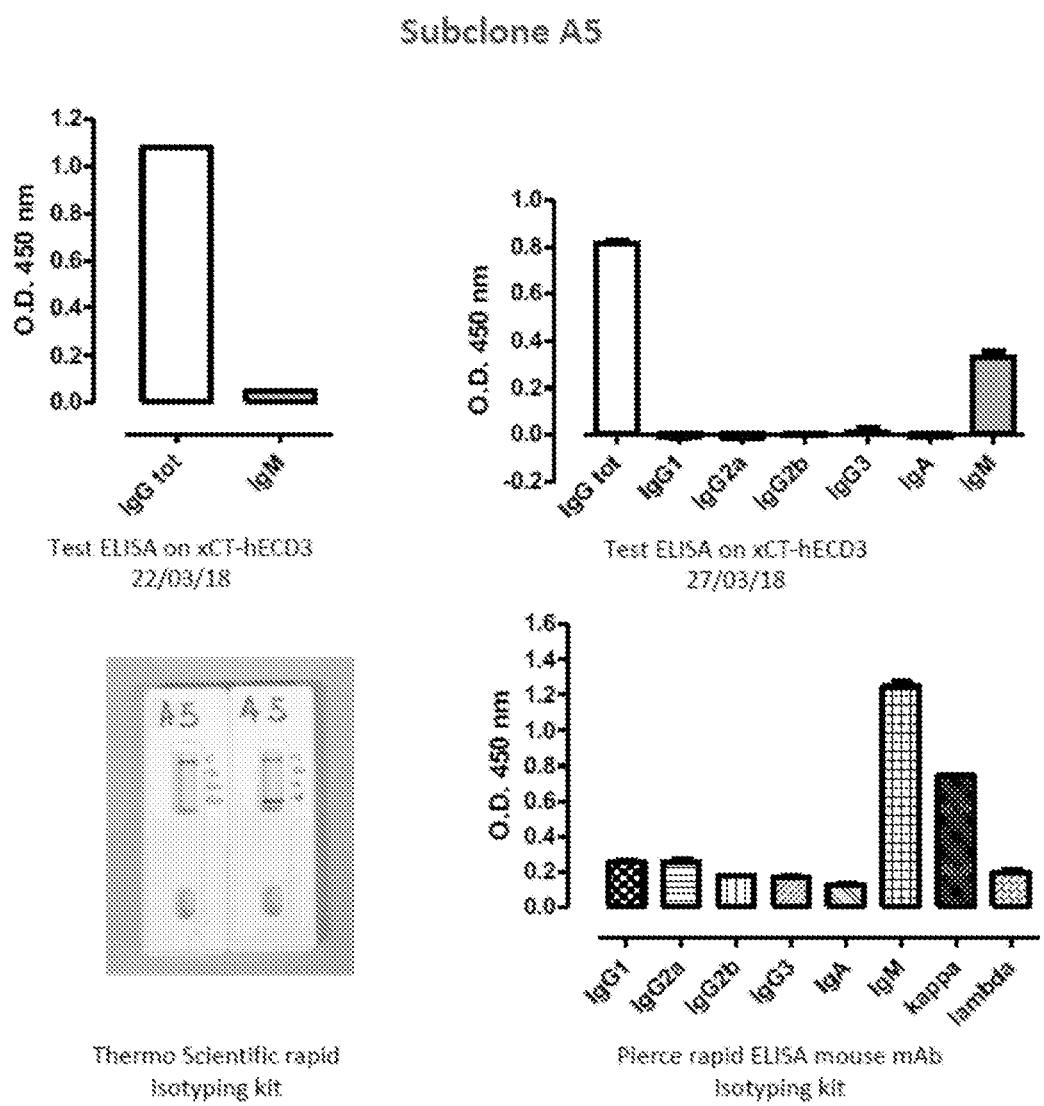
Figure 14:
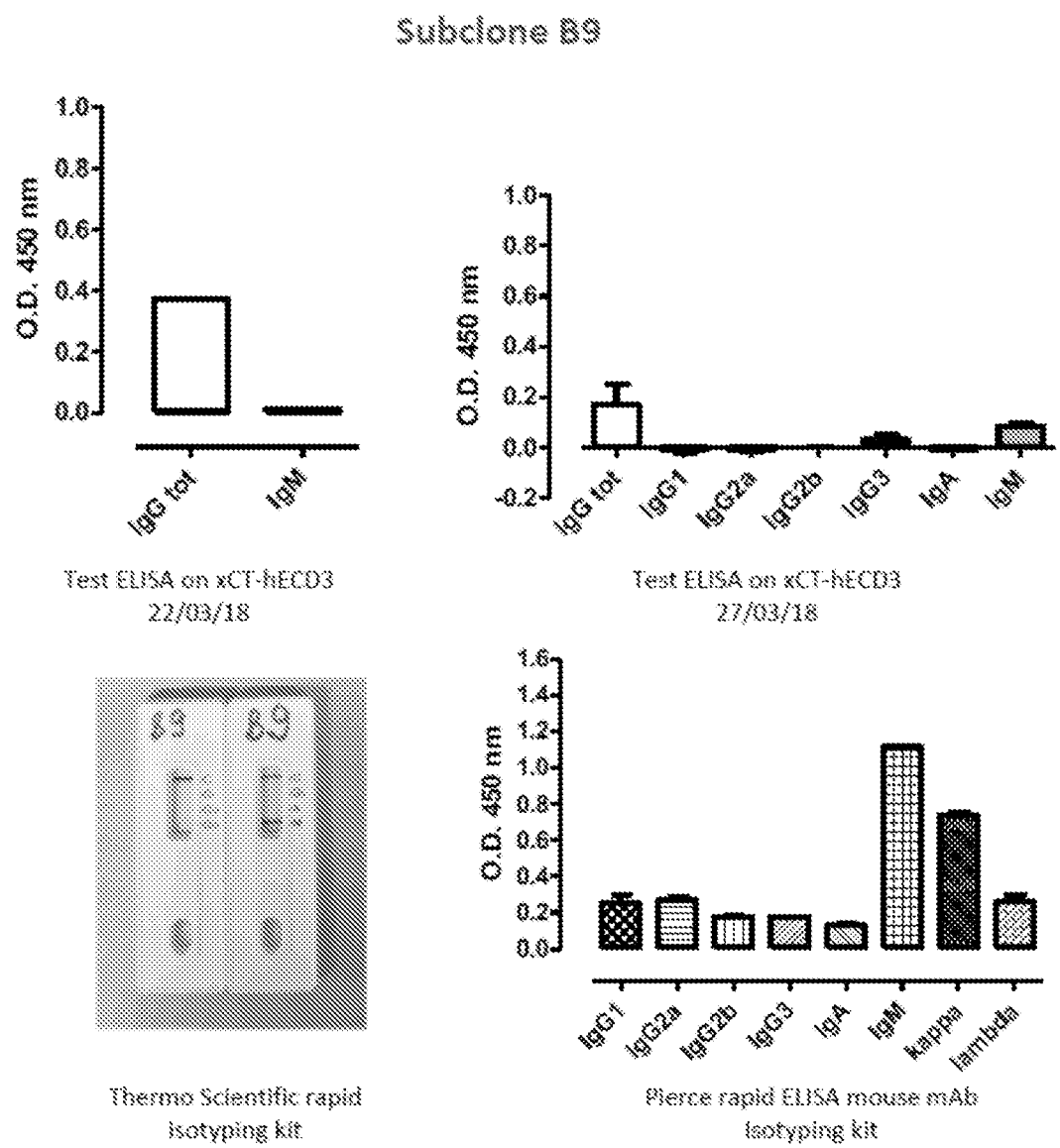
Figure 15:
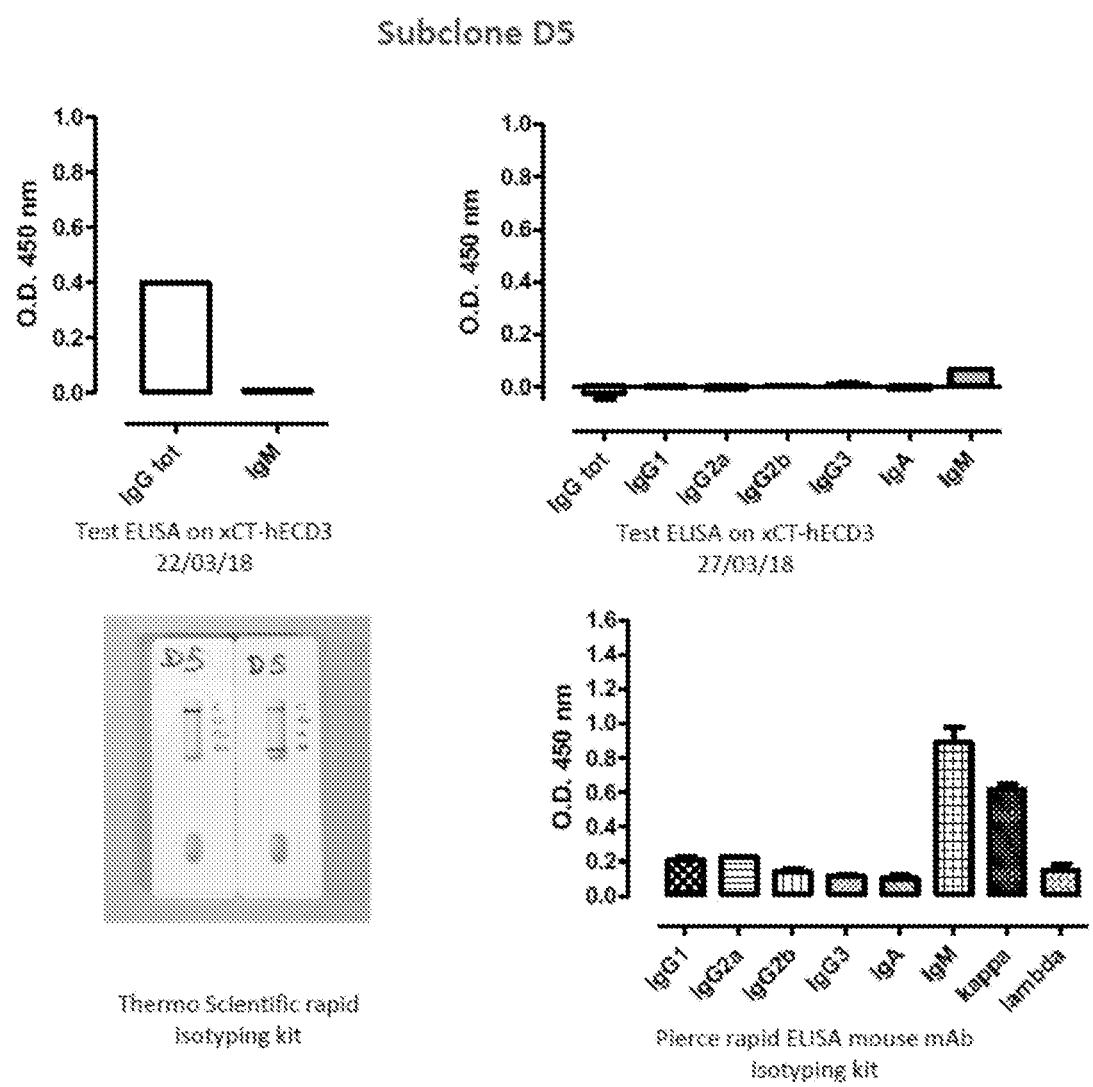
Figure 16:
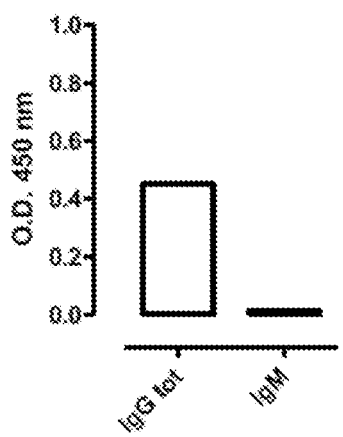
Figure 16:
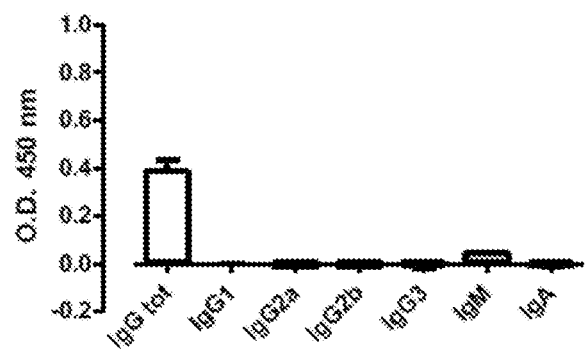
Figure 16:
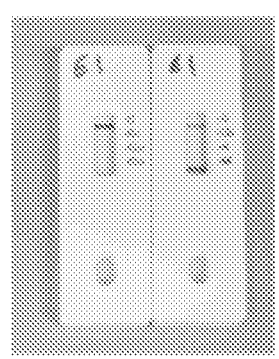
Figure 16:
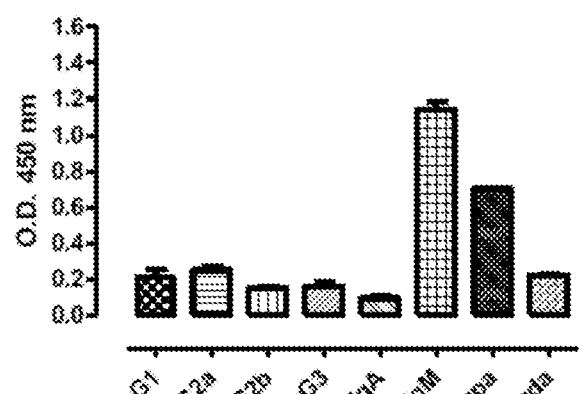

FIG. 11 Data suggest that the 11D1/H10 was not a clone, but contains cells producing different Ig isotypes. For this reason, 11D1/H10 was subcloned, obtaining 30 new clones, then tested by ELISA.

FIGS. 12-16 Five of these clones resulted secreting Ig (ELISA O.D. 450≥0.400) against xCT. The culture supernatants from these subclones (FIG. 12—A1, FIG. 13—A5, FIG. 14—B9, FIG. 15—D5, and FIG. 16—E1) were tested for the presence of anti-xCT Ig or Ig isotypes.

DESCRIPTION

Certain cancer cells express abnormally high levels of the plasma cell membrane components of the system $x_c^-$ heterodimeric amino acid transporter specific for cystine/glutamate exchange. System $x_c^-$ imports L-cystine into the intracellular compartment of a cell, which requires L-cystine for the synthesis of glutathione (L-γ-glutamyl-L-cysteinylglycine, referred to herein as "GSH"), an antioxidant that is important for cell survival under hypoxic conditions, such as those that exist in a tumor environment. The structure of System $x_c^-$ imports is composed of SLC7A11, a catalytic subunit that gives the transporter its specificity for cystine, and SLC3A2, a regulatory subunit. SLC7A11 and SLC3A2 are also known in the field as xCT and 4F2hc/CD98, respectively.

Because tumor cells, and other abnormally rapidly dividing or differentiating cells require greater amounts of GSH to handle higher levels of oxidative stress, such cells more highly express system $x_c^-$ components for the importation of cystine than do normal cells under normal conditions. As such, the invention takes advantage of the increased expression of system $x_c^-$ components by hyperproliferative cells by providing an anti-xCT antibody that targets the xCT component of target cells (e.g., cancer stem cells (CSC).

I. Therapeutic Antibodies

Certain embodiments of the present invention is directed to an antibody, e.g., a monoclonal antibody, that recognizes human xCT or a cell expressing the same. The invention is also directed to a hybridoma cell line that produces the antibody, and to methods of treating cancer using the antibody. The antibody recognizes and specifically binds human xCT in its native form, which is expressed on the cellular membrane.

The term "antibody" is used herein in the broadest sense and refers generally to a molecule that contains at least one antigen binding site that immunospecifically binds to a particular antigen target of interest. The term "antibody" thus includes but is not limited to antibodies and variants thereof, fragments of antibodies and variants thereof, peptibodies and variants thereof, and antibody mimetics that mimic the structure and/or function of an antibody or a specified fragment or portion thereof, including single chain antibodies and fragments thereof. The term "antibody," thus includes full-length antibodies or their variants as well as fragments thereof. Binding of an antibody to a target can cause a variety of effects, such as but not limited to, it modulates, decreases, increases, antagonizes, agonizes, mitigates, alleviates, blocks, inhibits, abrogates or interferes with at least one target activity or binding, or with receptor activity or binding, in vitro, in situ, and/or in vivo.

The present invention, thus, encompasses antibodies capable of binding to xCT or portions thereof, including but not limited to Fab, Fab' and F(ab')₂, facb, pFc', Fd, Fv or scFv fragments; diabodies; linear antibodies; single-chain antibody molecules; and multispecific antibodies formed from antibody fragments.

Accordingly, antibody is used in the broadest sense and specifically covers, for example, single anti-xCT monoclonal antibodies (including agonist, antagonist, and neutralizing antibodies), anti-xCT antibody compositions with polyepitopic specificity, single chain anti-xCT antibodies, and fragments of anti-xCT antibodies.

The term "monoclonal antibody" as used herein refers to an antibody obtained from a population of substantially homogeneous antibodies, i.e., the individual antibodies comprising the population are identical except for possible naturally occurring mutations that may be present in minor amounts. In certain aspects a monoclonal antibody that specifically binds an xCT peptide is described.

Specific antibody fragments of the present invention include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, *Nature* 341:544-46) which consists of a single variable, (v) isolated CDR regions, (vi) F(ab')2 fragments, a bivalent fragment comprising two linked Fab fragments, (vii) single chain Fv molecules (scFv), wherein a VH domain and a VL domain are linked by a peptide linker which allows the two domains to associate to form an antigen binding site (Bird et al., 1988, *Science* 242:423-26, Huston et al., 1988, *Proc. Natl. Acad. Sci. U.S.A.* 85:5879-83), (viii) bispecific single chain Fv (WO 03/11161) and (ix) "diabodies" or "triabodies", multivalent or multispecific fragments constructed by gene fusion (Tomlinson et. al., 2000, *Methods Enzymol.* 326:461-79; WO94/13804; Holliger et al., 1993, *Proc. Natl. Acad. Sci. U.S.A.* 90:6444-48). The antibody fragments may be modified. For example, the molecules may be stabilized by the incorporation of disulfide bridges linking the VH and VL domains (Reiter et al., 1996, Nature Biotech. 14:1239-1245).

"Fv" is the minimum antibody fragment that contains a complete antigen-recognition and binding site. This region consists of a dimer of one heavy-chain and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified to greater than 95% by weight of antibody as determined by the Lowry method, and most preferably more than 99% by weight; to a degree sufficient to obtain at least 15 residues of N-terminal or internal amino acid sequence by use of a spinning cup sequenator; or to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "native sequence xCT polypeptide" comprises a polypeptide having the same amino acid sequence as the corresponding xCT polypeptide derived from nature, e.g., SEQ ID NO: 1. Such native sequence xCT polypeptides can be isolated from nature or can be produced by recombinant or synthetic means. The term "native sequence xCT polypeptide" specifically encompasses naturally occurring truncated or secreted forms of the specific xCT polypeptide (e.g., a loop or partial loop sequence), naturally-occurring variant forms (e.g., alternatively spliced forms) and naturally-occurring allelic variants of the polypeptide.

The terms "individual," "subject," and "patient," used interchangeably herein, refer to an animal, preferably a mammalian (including non-primate and primate), including, but not limited to, murines, simians, humans, mammalian farm animals (e.g., bovine, porcine, ovine), mammalian sport animals (e.g., equine), and mammalian pets (e.g., canine and feline); preferably the term refers to humans.

As used herein, the terms "treatment", "treating", and the like, refer to obtaining a desired pharmacologic or physiologic effect. The effect may be therapeutic in terms of a partial or complete cure for a disease, symptom, and/or adverse effect attributable to the disease. "Treatment," as used herein, includes administration of a compound of the present invention for treatment of a disease or condition in a mammal, particularly in a human, and includes: (a) inhibiting the disease, i.e., arresting its development; (b) providing palliative care, i.e., reducing and preventing the suffering of a patient; and (c) relieving the disease, i.e., causing regression of the disease or disorder or alleviating symptoms or complications thereof. Dosage regimens may be adjusted to provide the optimum desired response.

"Framework" or "FR" residues are those variable-domain residues other than the hyper variable region (HVR) residues as herein defined. A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al, supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain preexisting amino acid sequence changes. In some embodiments, the number of preexisting amino acid changes are 10 or less, 9 or less, 8 or less, 7 or less, 6 or less, 5 or less, 4 or less, 3 or less, or 2 or less.

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant ($K_D$) of $<1\times10^{-6}$ M, $<1\times10^{-7}$ M, $<1\times10^{-8}$ M, $<1\times10^{-9}$ M, or $<1\times10^{-10}$ M.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas human monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). Unless indicated otherwise herein, the numbering of the residues in an immunoglobulin heavy chain is that of the EU index as in Kabat et al, supra. The "EU index as in Kabat" refers to the residue numbering of the human IgG1 EU antibody.

"Binding affinity" generally refers to the strength of the sum total of non-covalent interactions between a single binding site of a molecule (e.g., of an antibody) and its binding partner (e.g., an antigen). Unless indicated otherwise, as used herein, "binding affinity", "bind to", "binds to" or "binding to" refers to intrinsic binding affinity that reflects a 1:1 interaction between members of a binding pair (e.g., antibody Fab fragment and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity.

The "$K_D$" or "$K_D$ value" according to this invention is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al, (1999) *J. Mol. Biol* 293:865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest. The Fab of interest is then incubated overnight; however, the incubation may continue for a longer period (e.g., 65 hours) to ensure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 µl/well of scintillant (Micro Scint-20; Packard) is added, and the plates are counted on a Topcount gamma counter (Packard) for ten minutes. Concentrations of each Fab that give less than or equal to 20% of maximal binding are chosen for use in competitive binding assays.

The term "conformational epitope" as used herein refers to amino acid residues of the antigen that come together on the surface when the polypeptide chain folds to form the native protein.

A. Monoclonal Antibodies

The anti-xCT antibodies may be monoclonal antibodies. Monoclonal antibodies may be prepared using hybridoma methods, such as those described by Kohler and Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

An immunizing agent typically includes the xCT polypeptide, peptide, or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding (1986) *Monoclonal Antibodies: Principles and Practice*, Academic Press, pp. 59-103). Immortalized cell lines may be transformed mammalian cells, particularly myeloma cells of rodent, bovine and human origin. Rat or mouse myeloma cell lines may be employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. (1984) Immunol. 133:3001; Brodeur et al. (1987) Monoclonal Antibody Production Techniques and Applications, Marcel Dekker, Inc., New York, pp. 51-631).

The culture medium in which the hybridoma cells are cultured can then be assayed for the presence of monoclonal antibodies directed against xCT or the xCT peptides described herein. The binding specificity of monoclonal antibodies produced by the hybridoma cells can be determined by inmunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980) Anal. Biochem. 107:220.

The monoclonal antibodies secreted by the subclones may be isolated or purified from the culture medium or ascites fluid by conventional immunoglobulin purification procedures such as protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures, e.g., by using oligonucleotide probes that are capable of binding specifically to genes encoding the heavy and light chains of murine antibodies. The hybridoma cells of the invention serve as a preferred source of such DNA. Once isolated, the DNA may be placed into expression vectors, which are then transfected into host cells, such as, simian COS cells, Chinese hamster ovary (CHO) cells, or myeloma cells that do not otherwise produce immunoglobulin protein, in order to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bifunctional or multifunctional antibody with non-identical antigenic binding specificities, each of which may be monovalent, bivalent, or multivalent.

The antibodies of the present invention may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

The anti-xCT monoclonal antibodies of the invention may be whole or an antigen-binding fragment of the antibody that binds to a xCT polypeptide or peptide, preferably a native sequence xCT polypeptide. Furthermore, in a preferred embodiment the monoclonal antibody is identified as having recognition of a xCT protein from at least one cancer cell line.

In one non-limiting embodiment the monoclonal antibody is produced by hybridoma cell line, wherein said antibody or functional fragment thereof binds to a XCT protein and wherein said antibody or functional fragment thereof binds a CSC, neoplastic cell, or antigen thereof as said antibody or functional fragment thereof.

B. Human and Humanized Antibodies

The monoclonal antibodies of the present invention can be human or humanized to reduce the immunogenicity for use in humans. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) Nature 321:522; Riechmann et al. (1988) Nature 332:323; and, Presta (1992) Curr. Op. Struct. Biol. 2:593).

Methods for humanizing non-human antibodies are well known in the art. An example approach is to make mouse-human chimeric antibodies having the original variable region of the murine monoclonal antibodies, joined to constant regions of a human immunoglobulin. Chimeric antibodies and methods for their production are known in the art. See, e.g., Cabilly et al., European Patent EP0125023 (published Mar. 3, 2002); Taniguchi et al., European Patent EP0171496 (published May 26, 1993); Morrison et al., European Patent Application EP0173494 (published Jan. 18, 1986); Neuberger et al., International Publication No. WO/1986/01533, (published Mar. 13, 1986); Kudo et al., European Patent Application EP0184187 (published Jun. 11, 1986); Robinson et al., International Publication No. WO/1987/002671 (published May 7, 1987); Liu et al. (1987) Proc. Natl. Acad. Sci. USA 84:3439; Sun et al. (1987) Proc. Natl. Acad. Sci. USA 84:214; Better et al. (1988) Science 240:1041. These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

A chimeric antibody can be further humanized by replacing sequences of the Fv variable region which are not directly involved in antigen binding with equivalent sequences from human Fv variable regions. General methods for generating humanized antibodies are provided by Morrison, S. L., 1985, Science 229:1202-1207 by Oi et al., 1986, BioTechniques 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPIIbIIIa antibody producing hybridoma. The recombinant DNA encoding the chimeric antibody can then be cloned into an appropriate expression vector.

Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al. (1986) Nature 321:522; Riechmann et al. (1988) Nature 332:323; Verhoeyen et al. (1988) Science 239:1534), by substituting rodent CDRs or CDR sequences for the corresponding sequences of a human antibody. See also U.S. Pat. No. 5,225,539 and Beidler et al. 1988 J. Immunol. 141:4053. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol., 227:381 (1991); Marks et al. J. Mol. Biol., 222:581 (1991)). The techniques of Cole et al. and Boemer et al. are also available for the preparation of human monoclonal antibodies (Cole et al., Monoclonal Antibodies and Cancer Therapy, Alan R. Liss, p. 77 (1985) and Boerner et al. J. Immunol., 147(1):86 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al. Bio/Technology 10:779 (1992); Lonberg et al. Nature 368:856 (1994); Morrison, Nature 368:812 (1994); Fishwild et al. Nature Biotechnology 14:845 (1996); Neuberger, Nature Biotechnology 14:826 (1996); Lonberg and Huszar, Intern. Rev. Immunol. 13:65 (1995).

C. Pharmaceutical Compositions of Antibodies

In other embodiments there is provided a pharmaceutical composition including an antibody as described above together with a pharmaceutically acceptable carrier, diluent or excipient.

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of an antibody, or mixture of antibodies.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents, for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions may further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents, and/or preservatives. Alternatively, compositions of the present invention may be formulated as a lyophilisate.

While any suitable carrier known to those of ordinary skill in the art may be employed in the compositions of this invention, the type of carrier will typically vary depending on the mode of administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation which can be formulated in such a manner as to permit a sustained release of the active ingredient. An exemplary composition may comprise antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions, or solid or powder forms suitable for reconstitution with suitable vehicles, including by way of example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers, or other known encapsulating technologies.

The pharmaceutical compositions described herein may be presented in unit-dose or multi-dose containers, such as sealed ampules or vials. Such containers are typically sealed in such a way to preserve the sterility and stability of the formulation until use. In general, formulations may be stored as suspensions, solutions or emulsions in oily or aqueous vehicles, as indicated above. Alternatively, a pharmaceutical composition may be stored in a lyophilized condition requiring only the addition of a sterile liquid carrier immediately prior to use.

D. Uses for Anti-xCT Antibodies

The anti-xCT antibodies of the invention have various utilities. In one embodiment, an anti-xCT is provided for use in a method of treatment of a disease, such as cancer. The method of the invention preferably includes the step of providing an antibody or xCT antigen-binding fragment thereof, as described above, to a subject requiring said treatment.

Methods of immunotargeting cancer cells using antibodies or antibody fragments are well known in the art. U.S. Pat. No. 6,306,393, for instance, describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic or other agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include, for example, complement-mediated cytolysis, antibody-dependent cellular cytotoxicity (ADCC) modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

The antibodies can also be conjugated to toxic, chemotherapeutic, or therapeutic agents, such as radioligands or cytosolic toxins, and may also be used therapeutically to deliver the toxic or therapeutic agent directly to tumor cells.

Treatment is meant to include therapeutic, prophylactic, palliative, or suppressive treatment for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

In certain aspects, the therapeutic preparations can use nonmodified antibodies or antibodies conjugated with a therapeutic compound, such as a toxin or cytotoxic molecule, depending on the functionality of the antibody. Generally, when nonmodified antibodies are used, they will typically have a functional Fc region. By "functional Fc region" herein is meant a minimal sequence for effecting the biological function of Fc, such as binding to Fc receptors, particularly FcγR (e.g., Fcγ RI, FcγRII, and Fcγ RIII).

Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation. In this regard, polyclonal antibodies, or mixtures of monoclonals will be advantageous because they will bind to different epitopes and, thus, have a higher density of Fc on the cell surface as compared to when a single monoclonal antibody is used. Of course, to enhance their effectiveness in depleting targeted cells, or where non-modified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. The antibodies and antibody compositions of the invention may include, for example, PEGylated antibodies and/or pretargeting constructs of the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the subject will vary depending upon what is being administered, the purpose of the administration, such as prophylaxis or therapy, the state or condition of the subject, the manner of administration, the number of administrations, interval between administrations, and the like. These can be determined empirically by those skilled in the art and may be adjusted for the extent of the therapeutic response. Factors to consider in determining an appropriate dose include, but are not limited to, size and weight of the subject, the age and sex of the subject, the severity of the symptom, the stage of the disease, method of delivery, half-life of the antibodies, and efficacy of the antibodies. Stage of the disease to consider includes whether the disease is acute or chronic, relapsing or remitting phase, and the progressiveness of the disease. Determining the dosages and times of administration for a therapeutically effective amount is well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al. (1999) Semin. Oncol. 26.suppl. 12:60 describes in vitro measurements of antibody dependent cellular cytotoxicity. A dose can then be formulated in animal models to generate a circulating concentration or tissue concentration, including that of the IC50 as determined by the cell culture assays.

In addition, the toxicity and therapeutic efficacy are generally determined by cell culture assays and/or experimental animals, typically by determining the LD50 (lethal dose to 50% of the test population) and ED50 (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences, for example, in the case of a chimeric or humanized antibody. Within certain embodiments, an initial high dose of antibody is administered such that a degree of immunological tolerance to the therapeutic antibody is established. The tolerizing dose is sufficient to prevent or reduce the induction of an antibody response to repeat administration of the committed progenitor cell specific antibody.

Ranges for the tolerizing dose are, for example, between 10 mg/kg body weight to 50 mg/kg body weight, inclusive. In some embodiments, ranges for the tolerizing dose are between 20 and 40 mg/kg, inclusive. In still other embodiments, ranges for the tolerizing dose are between 20 and 25 mg/kg, inclusive.

Within these therapeutic regimens, the therapeutically effective dose of antibodies may be administered in the range of 0.1 to 10 mg/kg body weight, inclusive. In certain embodiments, therapeutically effective doses are in the range of 0.2 to 5 mg/kg body weight, inclusive. In other embodiments, therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

Antibody compositions may be formulated for any appropriate manner of administration, including for example, oral, nasal, mucosal, intravenous, intraperitoneal, intradermal, subcutaneous, and intramuscular administration.

For the purposes of this invention, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously.

The compositions may be administered once or several times. In some embodiments, the compositions may be administered once per day, a few or several times per day, or even multiple times per day, depending upon, among other things, the indication being treated and the judgment of the prescribing physician.

Administration of the compositions may also be achieved through sustained release or long-term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the invention contemplates the administration of single monoclonal antibodies and any antibody that recognizes the particular antigens recognized by these antibodies, as well as combinations, of different monoclonal antibodies. Two or more monoclonal antibodies may provide an improved effect compared to a single antibody. Alternatively, a combination of an antibody with an antibody that binds a different antigen may provide an improved effect compared to a single antibody. Such monoclonal antibodies cocktails may have certain advantages inasmuch as they contain monoclonal antibodies, which exploit different effector mechanisms or combine directly cytotoxic monoclonal antibodies with monoclonal antibodies that rely on immune effector functionality. Such monoclonal antibodies in combination may exhibit synergistic therapeutic effects.

In another embodiment, anti-xCT antibodies may be used in diagnostic assays for xCT, e.g., detecting its expression in specific cells, tissues, or serum.

"Detecting" refers to determining the presence, absence, or amount of an analyte in a sample, and can include quantifying the amount of the analyte in a sample or per cell in a sample.

"Diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

The present invention relates to diagnostic assays, both quantitative and qualitative for detecting levels of xCT polypeptide in cells, tissues and bodily fluids, including determination of normal and abnormal levels. Assay techniques that can be used to determine levels of a polypeptide, such as xCT of the present invention, in a sample derived from a host are well-known to those of skill in the art. Such assay methods include, but are not limited to, radioimmunoassays, immunohistochemistry assays, in situ hybridization assays, competitive-binding assays, Western Blot analyses and ELISA assays. Among these, ELISAs are frequently used to detect a gene's expressed protein in biological fluids. An ELISA assay initially comprises preparing an antibody specific to xCT, preferably a monoclonal antibody. In addition, a reporter antibody generally is prepared which binds specifically to xCT. The reporter antibody is attached to a detectable reagent such as a radioactive, fluorescent or enzymatic reagent, for example horseradish peroxidase enzyme or alkaline phosphatase.

The above tests can be carried out on samples derived from subjects' bodily fluids and tissue extracts (homogenates or solubilized tissue) such as from tissue biopsy and autopsy material. Levels of xCT, determined in cells and tissues from a patient suspected of suffering from cancer by measuring the polypeptide or by transcription levels, are compared to levels of xCT in normal or control cells or tissues. Increased levels of xCT measured in the subject as compared to levels in the same cells, tissues, or bodily fluids obtained from normal, healthy individuals are indicative of cancer. By "increased levels" it is meant an increase in measured xCT levels in a subject as compared to xCT levels in the same normal cells or tissues. Detection of increased xCT levels is useful in the diagnosis of various cancers including, but not limited to, breast cancer, pancreatic cancer, prostate cancer, melanoma, colon cancer, lung cancer, and thyroid cancer.

Further, monitoring of xCT levels in a subject diagnosed with cancer is useful in determining the onset of metastases in cancers that have not yet metastasized and in determining the stage of the cancer. For example, detection of xCT can be used in a method of monitoring cancer in a subject that has not metastasized for the onset of metastasis. In this method, a subject suffering from a cancer that is not known to have metastasized is identified. xCT levels in a sample from the subject are then measured. These measured xCT levels are then compared with levels of xCT from a normal control sample. An increase in measured xCT levels in the subject versus the normal control is associated with a cancer that has metastasized.

The stage of cancer in a subject suffering from can also be determined. In this method a subject suffering from cancer is identified. xCT levels in a sample of tissue from the patient are measured to establish a baseline xCT level for said patient. xCT levels in samples of the same tissue are then determined at subsequent time periods such as scheduled check-ups with the subject's physician. Measured xCT levels are then compared with the baseline xCT levels for the patient. In this method, an increase in measured xCT levels in the subject versus baseline xCT levels in the subject is associated with a cancer that is progressing and a decrease in measured xCT levels versus baseline xCT levels is associated with a cancer that is regressing or in remission. Increases in measured xCT levels as compared to baseline xCT levels established for the subject may also be indicative of metastases.

In one embodiment, xCT immunohistochemistry functions as an "index diagnostic" to assign risk based on the presence of xCT expression. Therefore, based on this and other parameters (e.g., size of lesion), one can determine whether or not different therapeutic modalities (i.e., chemotherapy, radiation therapy, surgery) should be used. In a related aspect, methods for monitoring progression of pre-malignancy into a malignant phenotype are disclosed. For example, by using serial sampling (i.e., biopsy) of the tissue and observing the state of xCT expression in the lesions, one can determine whether or not the premalignancies are progressing in a way that would indicate whether therapeutic intervention is advised or is successful.

One aspect of the invention is a method to determine the likelihood of a group of cells to become cancerous, e.g., the cells or glands become premalignancies or progress to cancerous lesions. The invention utilizes an agent, such as an antibody, that specifically binds to xCT protein to assess levels of xCT in tissue and cells. xCT expression in cells and tissue may also be assessed using nucleic acid analysis, such as selective amplification, or hybridization methods. A level of xCT above normal or control levels, indicates an increased likelihood that premalignant disease is present, i.e., that the cells or tissues are premalignant.

E. Antibody Kits

Antibody kits are provided which contain the necessary reagents to carry out the treatments or assays of the present invention. The kit may include one or more compartments, each to receive one or more containers such as: (a) a first container comprising one of the components of the present invention described above; and (b) one or more other containers comprising one or more of the following: wash reagents, reagents capable of detecting presence of the antibody or peptide.

The containers allow the efficient transfer of reagents from one compartment to another compartment such that the samples and reagents are not cross-contaminated, and the agents or solutions of each container can be added in a quantitative fashion from one compartment to another.

The kit typically contains containers that may be formed from a variety of materials, such as glass or plastic, and can include for example, bottles, vials, syringes, and test tubes. A label typically accompanies the kit, and includes any writing or recorded material, which may be in electronic or computer readable form (e.g., disk, optical disc, or tape) providing instructions or other information for used of the contents of the kit. The label indicates that the formulation is used for diagnosing or treating the disorder of choice.

One skilled in the art will readily recognize that the disclosed antibodies of the present invention can be readily incorporated into one of the established kit formats that are well known in the art.

II. Anti-Cancer Therapies

In certain embodiments the compositions and methods described herein in can be administered in conjunction or combination with other anti-cancer therapies for the treatment of cancer. Therapeutically effective doses can be determined by one of skill in the art and will depend on the severity and course of the disease, the patient's health and response to treatment, the patient's age, weight, height, sex, previous medical history and the judgment of the treating physician.

In some methods of the invention, the cancer cell is a tumor cell. The cancer cell may be in a patient. The patient may have a solid tumor. In such cases, embodiments may further involve performing surgery on the patient, such as by resecting all or part of the tumor. xCT VLPs described herein can be administered before, during, or after an anti-cancer treatment. Anti-cancer treatments may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Anti-cancer compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, docetaxel, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

In some embodiments, the cancer that is administered the composition(s) described herein may be a bladder, blood, bone, bone marrow, brain, breast, colorectal, esophagus, gastrointestine, head, kidney, liver, lung, nasopharynx, neck, ovary, pancreas, prostate, skin, stomach, testicular, tongue, or uterus cell. In certain aspects the cancer is breast cancer.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

To investigate whether xCT VLPs induced antibodies could affect xCT function and BCSC biology, IgG was purified from the sera of control VLP- or xCT VLP-treated mice. BCSC enriched cells from the indicated sTNBC cell lines were incubated with purified antibodies and 3D cultures were used to analyze BCSC self-renewal and proliferation while the frequency of aldefluor positive cells (a marker of BCSC phenotype) in the spheres and intercellular ROS levels (an indication of xCT function) were measured by FACS. As observed with other methods of xCT inactivation (siRNA, SASP treatment and DNA vaccination, xCT VLPs induced IgG antibodies decreased BCSC self-renewal, proliferation and increased ROS levels (FIG. 1). There was also a significant decrease in the number of BCSC in the tumorspheres that did form in cultures treated with xCT VLP induced antibodies.

FIG. 1. Shows that AX09 (xCT epitope displayed on an RNA bacteriophage VLP)-induced antibodies affect BCSC biology and inhibit xCT function in human cells. Passage 1 MDA-MB-231 derived tumorspheres were dissociated and replated ($4 \times 10^5$/well) with purified IgG isolated from control VLP or AX09 treated mice at 50 µg/ml in sphere medium. Media containing no IgG was used as a control. Cultures were analyzed five days later and each assay was done in triplicate. Error bars represent standard deviation and ** represents a p-value from student's t-test of <0.01. (A) To analyze BCSC self-renewal, the number of secondary tumorspheres that formed in 3D culture were counted and plotted as number of spheres/$10^3$ cells plated. (B) BCSC proliferation was assessed with acquired sphere images and measurement of mean sphere diameter was calculated using ImageJ software. (C) The ability of AX09 immune sera to inhibit xCT function was evaluated by measuring intercellular ROS levels. Dissociated spheres were incubated with 2,7 dihydrodichlorofluorescein diacetate and the ROS levels were evaluated by FACS. (D) To determine the frequency of BCSC in the tumorspheres, spheres were dissociated into single cell suspensions and analyzed for aldehyde dehydrogenase activity by incubating cells with ALDEFLUOR and analyzing cells by FACS. The percentage of ALDH positive cells (indicative of cancer stem/progenitor cells) were plotted.

Additional data with purified IgG incubated with triple negative breast cancer derived stem cells. Mouse TUBO derived cancer stem cells with both IgG purified from ECD6 and ECD3 VLPs. Mouse 4T1 derived cancer stem cells with both IgG purified from ECD6 and ECD3 VLPs. Human HTC1806 derived cancer stem cells with both IgG purified from ECD6 and ECD3 VLPs. Human MB-MDA 231 derived cancer stem cells with both IgG purified from ECD6 and ECD3 VLPs.

Production of Monoclonal Antibodies

ECD3 Mab—Standard industry protocol are used to produce antibodies directed against ECD3 and ECD6. The immunization schedule is found below.

|  | 1st imm | 2nd imm | 3rd imm | test bleeding | 4th imm | 2nd test bleeding | 5th imm | 3rd test bleeding | 6th imm | 4th test bleeding | 7th imm | 5th test bleeding | Final boost |
|---|---|---|---|---|---|---|---|---|---|---|---|---|---|
| adjuvant | CPA | IFA | IFA |  | IFA |  | IFA |  | IFA |  | IFA |  | Without adjuvant |
| VLP | 10 | 10 | 10 |  | 10 |  | 10 |  | 10 |  | 10 |  | 10 ug/mouse |

-continued

|  | 1st imm | 2nd imm | 3rd imm | test bleeding | 4th imm | 2nd test bleeding | 5th imm | 3rd test bleeding | 6th imm | 4th test bleeding | 7th imm | 5th test bleeding | Final boost |
|---|---|---|---|---|---|---|---|---|---|---|---|---|---|
| inject site | SC | SC | SC |  | SC |  | SC |  | SC |  | SC |  | IP |
| inject day | 0 | 21 | 35 | 45 | 49 | 59 | 63 | 73 | 77 | 87 | 91 | 101 |  |

At the end of Phase II, no positive hybridoma clones were found for ECD6. The rest of this section documents ECD3 production.

ELISA after Final Boost—
(1) Antigen coating: Step1: streptavidin in 1×PBS, 10.0 μg/ml; Coating amount: 50 μL/well, 37° C. 2 hours; then with three washings of the wells with 1×PBS; Step2: Biotinylated ECD3 Peptide for screening in 1×PBS, 10.0 μg/ml; Coating amount: 50 μL/well, 4° C. over night; then with three washings of the wells with 1×PBS. (2) Blocking: 5% BSA/PBS, 100 μL/well, RT 2 hours; (3)Primary Antibody: Mouse sera from 6th immunization. 50 μL/well, RT 2 hours. (4) Secondary Antibody: HRP labeled anti-IgG: SIGMA, Cat #: A0168, Lot NO: 097K4831; Dilution: 1:9,000, 50 μL/well, RT 2 hours. (5) Substrate solution: TMB, 100 μL/well, 37° C. 10 min, OD read in 450 nm; and (6) OD Reading Result (double wells):

| Mouse No. | Anti-serum | | | | |
|---|---|---|---|---|---|
| Dilution | 1 | 2 | 3 | 4 | 5 |
| 1:10³ | 0.096 | 0.187 | 0.197 | 0.132 | 0.352 |
|  | 0.117 | 0.184 | 0.190 | 0.119 | 0.344 |
| 1:10⁴ | 0.052 | 0.072 | 0.073 | 0.068 | 0.087 |
|  | 0.071 | 0.073 | 0.078 | 0.068 | 0.089 |
| 1:10⁵ | 0.054 | 0.042 | 0.041 | 0.037 | 0.047 |
|  | 0.052 | 0.046 | 0.047 | 0.045 | 0.044 |

| Mouse No. | Pre-immune serum | | | | |
|---|---|---|---|---|---|
| Dilution | 1 | 2 | 3 | 4 | 5 |
| 1:10³ | 0.194 | 0.195 | 0.196 | 0.197 | 0.194 |
|  | 0.195 | 0.192 | 0.194 | 0.193 | 0.192 |
| 1:10⁴ | 0.094 | 0.096 | 0.095 | 0.095 | 0.094 |
|  | 0.091 | 0.092 | 0.090 | 0.092 | 0.093 |
| 1:10⁵ | 0.042 | 0.041 | 0.039 | 0.040 | 0.043 |
|  | 0.040 | 0.038 | 0.041 | 0.037 | 0.040 |

Agilvax has optimized peptide ELISAs for use in evaluating xCT antibody responses. Therefore, optimized peptide ELISA protocols were used to test the final bleed and to choose an animal to move forward with.

C. ECD3 peptide (containing a reactive Cysteine residue on its C-terminus) was added to wells at 2 μg/well and incubated overnight at 4° C. Plates were blocked with 0.5% milk in PBS for 1 hour at room temperature and 3-fold dilutions of sera (starting at 1:500 and ending at 1:13500) were added to each well and incubated for 2 hours. Wells were probed with HRP-labeled goat anti-mouse IgG (1:5000) for 1 hour. The reaction was developed with TMB for 1 hour and stopped using 1% HCl. Reactivity of sera for ECD3 was determined by measuring optical density at 450 nm. The controls are from BALB/c female mice (4/6 weeks old) that were immunized (intramuscular) with 5 μg of ECD3 VLP in the absence of exogenous adjuvant and given a boost 14 days later with the same formulation. 14 days later sera was collected. This represents the range of typical antibody responses using a typical immunization protocols with ECD3.

From this data, animal #5 was chosen for hybridoma fusion and subsequent testing of IgG clones using ECD3 ELISA.

Testing of ECD3 Hybridoma Supernatants.
ECD3 (94653): All clones targeted against ECD3 VLPS and MST WT. One clone was positive for ECD3 VLPS and negative for MST WT. Also, all clones were weakly positive for biotinylated ECD3 Peptide. There were fewer than 50 clones.

VLP Monoclonal Antibody Production Immunization Protocol.

In this study, the immunization schedule and route of administration that produced the IgG antibodies that inhibited xCT function on the cancer stem cell studies are used. Groups of 5 female BALB/c mice (4-8 week old) are immunized with the various xCT VLPs by injecting 10 μg of VLP without adjuvant into the right caudal thigh muscle (IM), followed by a boost four weeks later.

Blood from submandibular vein is collected one day prior to boost and an aliquot of undiluted sera is used for ELISA along with an aliquot of preimmune sera from each animal. A second blood collection is done 2 weeks post boost and undiluted sera collected. If the titers are acceptable, ~10⁵,

| Peptide ELISA using E CD 3 peptide | | | | | | | | | | | | |
|---|---|---|---|---|---|---|---|---|---|---|---|---|
|  | E CD 3 Anti-sera (ProMab) | | | | | E CD 3 Preimmune Sera (ProMab) | | | | | IME | |
| Sera Dilution | Animal 1 | Animal 2 | Animal 3 | Animal 4 | Animal 5 | Animal 1 | Animal 2 | Animal 3 | Animal 4 | Animal 5 | CD3 Agilvax | None |
| 500 | 1.65 | 0.29 | 0.84 | 0.1 | 3.93 | 0.051 | 0.1 | 0.07 | 0.04 | 0.07 | 4.01 | 0.04 |
| 1.35E+04 | 0.05 | 0.04 | 0.04 | 0.03 | 0.08 | 0.04 | 0.04 | 0.04 | 0.07 | 0.04 | 0.42 | 0.04 |

Peptide ELISA:

ELISA plates were incubated with 1 μg avidin in PBS (pH 7.5) for 2 hours at 37° C. Following washing, SMPH was added to wells at 2 μg/well and incubated for 2 hours at 37° with optimized peptide ELISA, hybridoma fusion is done using splenocytes from the mouse with the best titer.

If the titer is below acceptable levels, one additional boost at week (7-8) is followed by one additional blood collection 2 weeks later will be done. Hybridoma fusion is done using splenocytes from the mouse with the best titer.

xCT DNA Immunization Followed by VLP Boost Mab Production.

A different approach can be used for the development of therapeutic xCT ECD targeted Mabs.

In vivo electroporation using the mouse DNA plasmid-based vaccine is performed in 8 BALB/c mice to initiate an overall xCT antibody response a second DNA plasmid boost occurred 10 days later. To boost and target the antibody response towards the xCT ECDs, VLPs displaying specific xCT ECD are used for immunization by injecting 10 μg of VLP without adjuvant into the right caudal thigh muscle (IM), followed by a boost four weeks later. 2 mice per xCT VLP are used for the boosts with the indicated VLPs.

Eight BALB/c Females are vaccinated on day 0 and day 10. The vaccine include (a) DNA electroporation of 50 μg/20 μL/mouse (Electroporator setting: low voltage; 2 pulses of 300 msec each; interval 25 sec, 150V) and (b) mouse. I.M. injection 10 μg VLP-ECD6 (total volume: 50 μL). Sera was collected before VLP boosts, VLP boosts=2. VLPs include AX09 (MS2 ECD6), Q-beta AX09 (ECD6), AX10 (MS2 NECD3), and MS2 NECD1.

Two weeks after final boost, blood from submandibular vein is collected 2 weeks post boost and sera is used for xCT screening. FACS analysis from sera is used to test if vaccination protocols elicited antibodies that bind to the extracellular regions of xCT from 4T1 cells. Hybridoma fusion is done using splenocytes from the mouse with the xCT binding characteristics.

xCT Monoclonal Antibody Data

VLP-Based Production of Monoclonal Antibodies.

For the development of a therapeutic xCT ECD3 targeted mAb, 10 BALB/c mice were primed with AX09-0M3 VLPs (NECD3) to initiate an antibody response. Depending on route of administration, animals received 2 or 3 AX09-0M3 VLP boosts, and peptide ELISA was performed on each test bleed to monitor antibody titer.

Standard industry protocols and Agilvax's standard protocol were used to produce antibodies directed against NECD3. Boost #3 (S.C./I.P.) and Boost #2 (I.M.) deviated from the standard 2 or 4-week intervals because of in-house testing. The immunization schedules are found below.

| | S.C./I.P. | | | | | | |
|---|---|---|---|---|---|---|---|
| | Pre-bleed | Prime | Boost #1 | Test Bleed #1 | Boost #2 | Test Bleed #2 | Boost #3 | Test Bleed #3 |
| VLP Injection Site | | 50 μg SC | 25 μg IP | | 25 μg SC | | 25 μg IP | |
| Injection Day | −4 | 0 | 14 | 21 | 28 | 35 | 104 | 111 |

Animals 5879 and 5880: Aluminum Adjuvant
Animals 5881 and 5882: CFA/IFA Adjuvant

| | I.M. | | | | | | |
|---|---|---|---|---|---|---|---|
| | Pre-bleed | Prime | Boost #1 | Test Bleed #1 | Boost #2 | Test Bleed #2 | Final Boost | Cell Fusion |
| VLP Injection Site | | 10 μg IM | 10 μg IM | | 10 μg IM | | 10 μg IM | |
| Injection Day | −4 | 0 | 28 | 42 | 104 | 111 | 193 | Final Boost +4 days |

Animals 5873-5878: No Adjuvant

Peptide ELISA after Boost #2 or #3.

ELISA Antigen: (A) N term Biotinylated ECD3 peptide (0.5 μg/mL, 100 μl/well); Coating Concentration (Streptavidin): 2 μg/mL; Coating Buffer: Phosphate Buffered Saline, pH 7.4; Secondary Antibody: Peroxidase-AffiniPure Goat Anti-Mouse IgG, Fcγ Fragment Specific (min X Hu,Bov,Hrs Sr Prot)

S.C./I.P. (Test Bleed #3)

| | Animal | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | | |
| | Dilution | | | | | | | | | | | | |
| | 1:1,000 | 1:2,000 | 1:4,000 | 1:8,000 | 1:16,000 | 1:32,000 | 1:64,000 | 1:128,000 | 1:256,000 | 1:512,000 | Blank | Titer | Coating |
| No.5879 | 2.806 | 3.013 | 2.879 | 2.873 | 2.723 | 2.329 | 2.048 | 1.471 | 0.974 | 0.589 | 0.046 | >1:512,000 | A |
| No.5880 | 2.878 | 3.036 | 2.841 | 2.799 | 2.606 | 2.351 | 1.732 | 1.407 | 0.931 | 0.528 | 0.047 | >1:512,000 | A |
| No.5881 | 3.216 | 3.291 | 3.117 | 2.833 | 2.617 | 2.308 | 1.822 | 1.341 | 0.937 | 0.626 | 0.056 | >1:512,000 | A |
| No.5882 | 2.893 | 3.002 | 2.982 | 2.671 | 2.285 | 1.945 | 1.436 | 0.986 | 0.673 | 0.421 | 0.050 | 1:512,000 | A |

I.M (Test Bleed #2)

| | Animal | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | | |
| | Dilution | | | | | | | | | | | | |
| | 1:1,000 | 1:2,000 | 1:4,000 | 1:8,000 | 1:16,000 | 1:32,000 | 1:64,000 | 1:128,000 | 1:256,000 | 1:512,000 | Blank | Titer | Coating |
| No.5873 | 3.055 | 2.985 | 2.775 | 2.706 | 2.503 | 2.154 | 1.571 | 1.082 | 0.667 | 0.387 | 0.048 | 1:512,000 | A |
| No.5874 | 3.022 | 3.043 | 2.908 | 2.781 | 2.609 | 2.256 | 1.803 | 1.112 | 0.823 | 0.471 | 0.047 | 1:512,000 | A |
| No.5875 | 3.125 | 2.941 | 2.879 | 2.769 | 2.499 | 2.065 | 1.568 | 1.017 | 0.647 | 0.371 | 0.049 | 1:512,000 | A |

I.M (Test Bleed #2)

| | Animal | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | | |
| | | | | | | Dilution | | | | | | | |
| | 1:1,000 | 1:2,000 | 1:4,000 | 1:8,000 | 1:16,000 | 1:32,000 | 1:64,000 | 1:128,000 | 1:256,000 | 1:512,000 | Blank | Titer | Coating |
| No.5876 | 3.123 | 2.967 | 2.981 | 2.766 | 2.491 | 2.148 | 1.611 | 1.163 | 0.734 | 0.415 | 0.049 | 1:512,000 | A |
| No.5877 | 3.011 | 2.952 | 2.870 | 2.685 | 2.506 | 2.134 | 1.717 | 1.227 | 0.817 | 0.466 | 0.049 | 1:512,000 | A |
| No.5878 | 2.820 | 2.867 | 2.813 | 2.619 | 2.412 | 2.141 | 1.734 | 1.167 | 0.811 | 0.459 | 0.047 | 1:512,000 | A |

The titer is the highest dilution with S/B (Signal/Blank) >=2.1

Agilvax has optimized peptide ELISAs for use in evaluating xCT antibody responses.

5 µg/mL; Coating Buffer: Phosphate Buffered Saline, pH 7.4; Secondary Antibody: Peroxidase-AffiniPure Goat Anti-Mouse IgG, Fcγ Fragment Specific (min X Hu,Bov,Hrs Sr Prot)

| VLP | Animal # | EPT (Sep 1, 2017) | EPT (Oct 24, 2017) | Route of Administration |
|---|---|---|---|---|
| AX09-0M3 | 5873 | 9.84E+06 | 9.84E+06 | i.m |
| AX09-0M3 | 5874 | 9.84E+06 | 9.84E+06 | i.m |
| AX09-0M3 | 5875 | 2.95E+07 | 9.84E+06 | i.m |
| AX09-0M3 | 5876 | 2.95E+07 | 3.28E+06 | i.m |
| AX09-0M3 | 5877 | 2.95E+07 | 9.84E+06 | i.m |
| AX09-0M3 | 5878 | 2.95E+07 | 9.84E+06 | i.m |
| AX09-0M3 | 5879 | 2.95E+07 | 9.84E+06 | s.c./i.p |
| AX09-0M3 | 5880 | 2.95E+07 | 9.84E+06 | s.c./i.p |
| AX09-0M3 | 5881 | 2.95E+07 | 9.84E+06 | s.c./i.p |
| AX09-0M3 | 5882 | 9.84E+06 | 3.28E+06 | s.c./i.p |

* Animals highlighted yielded positive results in IP experiment (see below)

From this data, Animal 5875 was chosen for hybridoma fusion using splenocytes and subsequent testing of IgG clones using ECD3 ELISA.

Peptide ELISA: 500 ng of N-terminal biotinylated hNECD3 peptide in a total of 200 µL were added to preblocked NeutrAvidin Coated 96-well ELISA plates and incubated overnight at 4° C. The following morning, plates were washed with Blocker BSA in PBS containing 0.05% Tween-20 and incubated with diluted sera (3-fold dilutions starting at 1:500 (9-1-17) or 1:1500 (10-24-17)) from individual animals for 2 hours with rocking at RT. Wells were washed with Blocker BSA. HRP-labeled goat anti-mouse IgG (1:5000) was added to wells and incubated at RT for 1 hour with rocking. Wells were washed and 200 µL of TMB Soluble (Calbiochem) were added and incubated at RT for 1 hr with rocking. The reaction was stopped with the addition of 100 µL 2% HCl and the plates were read at 450 nm. Endpoint titers were determined as the OD450 value that was 2 times over background (pooled pre-immune sera).

Immunofluorescence images of 4T1 epithelial cells incubated with sera from BALB/c mice vaccinated with AX09-0M3 were obtained. 4T1 epithelial cells plated overnight on glass coverslips were fixed in 4% formalin and incubated with sera at a 1:10 dilution for 1 hour at room temperature. The specific signal (green fluoresence) was detected after incubation with an Alexa Fluor488-conjugated anti-mouse IgG1 secondary antibody for 1 hour at room temperature. Nuclei were counterstained with DAPI (blue). Pre-serum samples from animals corresponding to the anti-serum samples above did not exhibit any specific signal.

Testing of AX09-0M3 Hybridoma Supernatants.

Primary and Confirmatory Peptide ELISA Screening.

ELISA Antigen: N term Biotinylated ECD3 peptide (0.5 µg/mL, 100 µl/well); Coating Concentration (Streptavidin):

Primary ELISA:

4800 clone supernatants were screened for binding to the hNECD3 peptide. A total of 388 positive clones from this screen (0D450>1.0) were selected for a second, confirmatory ELISA.

Confirmatory ELISA:

Clones were considered positive if the OD450>2.5. Positive clones were selected for expansion and supernatant collection. Supernatants from 146 parental clones were sent to Agilvax for further testing and to determine which clones will proceed to subcloning.

VLP Competition ELISA.

VLP Competition ELISA. AX09-0M3 or MS2 VLPs in a total of 100 µL were added to Immulon II 2HB 96-well ELISA plates and incubated overnight at 4° C. The following morning, plates were washed with 1×PBS and blocked with 0.5% milk in 1×PBS. During blocking, diluted clone supernatants (1:10) or control sera were incubated with excess MS2 VLPs. Plates were washed and incubated with the diluted clone supernatants or control sera for 1.5 hr with rocking at RT. After washing, HRP-labeled goat anti-mouse IgG was added to wells and incubated at RT for 1 hr with rocking. Wells were washed and 100 µL of TMB Soluble were added and incubated at RT for 1 hr with rocking. The reaction was stopped with the addition of 50 µL 2% HCl and the plates were read at 450 nm.

| OD450 on AX09-0M3 VLPs | # of Clones |
|---|---|
| >2.0 | 71 |
| >1.0 and <2.0 | 10 |
| >0.5 and <1.0 | 15 |
| >0.1 and <0.5 | 24 |
| <0.1 | 26 |

Primary screening by competition ELISA identified 71 clone supernatants that bound to AX09-0M3 VLPs and exhibited OD450 values of >2.0. Of these 71 clone supernatants, 55 supernatants gave an OD450 reading of >4.0, 11 supernatants gave an OD450 reading of >3.0 and <4.0, and 5 supernatants gave an OD450 reading of >2.0 and <3.0. With the goal to further selecting clone supernatants to move on to subcloning, all clones with an OD450 reading >0.100 were used in an IgG ELISA. The total amount of IgG determined by this ELISA was used to normalize the VLP ELISA OD450 readings.

IgG ELISA.

| Top 32 Clones | | |
|---|---|---|
| Clone ID | OD450-VLP ELISA | OD/IgG (ng) |
| 18C1 | 4.156 | 1.309 |
| 27D10 | 4.114 | 1.194 |
| 12D3 | 4.056 | 1.065 |
| 14B3 | 4.068 | 1.064 |
| 7C1 | 4.098 | 1.034 |
| 3H2 | 4.188 | 0.943 |
| 10E12 | 4.086 | 0.839 |
| 5E12 | 4.156 | 0.819 |
| 22G8 | 4.092 | 0.771 |
| 4H6 | 4.113 | 0.752 |
| 36H4 | 4.192 | 0.744 |
| 22D4 | 4.169 | 0.709 |
| 33C1 | 4.096 | 0.695 |
| 28H11 | 4.139 | 0.628 |
| 10G6 | 4.017 | 0.616 |
| 12E9 | 4.064 | 0.579 |
| 22A2 | 4.048 | 0.571 |
| 18C11 | 4.195 | 0.560 |
| 21D3 | 4.093 | 0.539 |
| 1A6 | 1.989 | 0.519 |
| 12D5 | 2.591 | 0.511 |
| 17H12 | 4.249 | 0.506 |
| 41D10 | 0.273 | 0.497 |
| 7F7 | 4.083 | 0.488 |
| 10A12 | 4.144 | 0.460 |
| 21B8 | 4.136 | 0.447 |
| 16A11 | 4.098 | 0.447 |
| 3D6 | 3.960 | 0.440 |
| 17F10 | 4.014 | 0.438 |
| 18G8 | 3.864 | 0.437 |
| 35G5 | 4.116 | 0.436 |
| 24B9 | 4.154 | 0.430 |

Diluted 120 clone supernatants (1:10 or 1:50) and mouse IgG standards were added to mouse IgG specific antibody coated wells and incubated for 2 hours with rocking at room temperature (RT). Wells were washed two times with 1× Wash Buffer. HRP-labeled goat anti-mouse detector antibody was diluted according to manufacturer's instructions, added to wells, and incubated at RT for 1 hour with rocking. After washing three times with 1× Wash Buffer, HRP Development Solution-TMB was added and incubated at RT. Color development was monitored and the plates were read at three different time points (~3, 7, and 11 min at 630 nm) to ensure that readings would be in range of the standard curve. At 15 min, the reaction was terminated with Stop Solution and the plates were read at 450 nm. A IgG standard curve with linear trendline was created in Excel (acceptable $R^2 > 0.98$) and used to determine the amount of IgG (ng)/clone supernatant. Mouse IgG standards were completed in duplicate while only a single well was used for the clone supernatants. Only the results for the top 32 are presented above.

The amount of IgG in the clone supernatants ranged from 0.549 ng to 12.510 ng (data not shown). After normalization (OD/ng IgG), 32 clones were identified using a cut-off of 0.430 and selected to move forward to subcloning. Prior to the initiation of subcloning, parental clones were revived and tested for binding to the hNECD3 peptide by ELISA.

Peptide ELISA-Parental Clone Supernatants.

Screening by peptide ELISA showed that all parental clone supernatants bound to hNECD3 peptide after cell revival and 28 of these clones exhibited OD450 values of >2.0. 28 clones were selected for one round of subcloning. To access binding to the target antigen, the resulting subclone supernatants were evaluated using a peptide ELISA (primary screen) and will be evaluated by FACS or IF (secondary screen).

Peptide ELISA-Subclone Supernatants.

One to three subclones were obtained from each parental clone. Screening by peptide ELISA showed that all 73 subclone supernatants bound to hNECD3 peptide after subcloning and exhibited OD450 values of >2.0. Subclone names=parental clone-subclone (i.e. 14B3-C3). To further characterize the subclones, the concentration of IgG and antibody isotype were determined.

IgG Concentration-Subclone Supernatants.

All clone supernatants contain detectable IgG. IgG concentration in the clone supernatants ranged from 0.057 µg/mL to 1.398 µg/mL. Subclone names=parental clone-subclone (i.e., 14B3-C3).

Isotype Analysis-Subclone Supernatants.

This analysis identified the presence of antibodies belonging to the IgG (kappa) isotype for each subclone tested except for one subclone, 10G6-B9, which was of the IgM (kappa) isotype. Within the IgG (kappa) subclones, 12 were identified as IgG1, 38 as IgG2a, and 22 as IgG2b.

Example 2

Generation of Monoclonal Antibodies Against xCT.

Female BALB/c mice (Charles River Laboratories), were maintained at the Molecular Biotechnology Center, University of Torino, and treated in accordance with the University Ethical Committee and European guidelines under Directive 2010/63. Vaccination consisted of one intramuscular electroporation of pVAX1-xCT DNA plasmid (coding for the full-length mouse xCT protein) as previously described (Lanzardo et al., 2016). Starting from the $10^{th}$ day after DNA vaccination, mice were boosted with AX09-0M3 VLP (against the third extracellular domain of human xCT protein; ECD3) monthly for 6 times. Mice were bled before the first VLP vaccination and then two weeks after each vaccination and sera collected and stored at −20° C. for subsequent analyses.

In order to test the functional effect of vaccination-induced antibodies, xCT cancer stem cell (CSC)-enriched 4T1-derived tumorspheres were incubated for 5 days with medium alone, the xCT pharmacological inhibitor sulfasalazine (SASP, 50 µM), or a 1:50 dilution of sera pooled from vaccinated or untreated mice. The sphere generating ability was reported as tumorsphere number/$10^3$ plated cells (FIG. 7). Sera from AX09-0M3 vaccinated mice were able to significantly reduce the sphere generating ability of 4T1 cells, suggesting the presence of antibodies able to interfere with xCT function.

To confirm the presence of anti-xCT antibody, sera samples collected after the $3^{rd}$ vaccination were then tested by ELISA. Briefly, 500 ng of N-terminal biotinylated hNECD3 peptide in a total of 200 µL were added to preblocked NeutrAvidin Coated 96-well ELISA plates and incubated overnight at 4° C. The following morning, plates were washed with Blocker BSA in PBS containing 0.05% Tween-20 and incubated with diluted sera (3-fold dilutions starting at 1:500 and ending at 1:8.86×10$^7$) from individual animals for 2 hours with rocking at RT. Wells were washed with Blocker BSA. HRP-labeled goat anti-mouse IgG (1:5000) was added to wells and incubated at RT for 1 hour with rocking. Wells were washed and 200 µL of TMB Soluble (Calbiochem) were added and incubated at RT for 1 hour with rocking. The reaction was stopped with the addition of 100 µL 2% HCl and the plates were read at 450 nm. Endpoint titers were determined as the OD450 value that was 2 times over background (untreated or MS2 sera). This represents the range of typical antibody responses using Agilvax's typical immunization protocols with ECD3. Serum from mouse B5 showed the higher end-point titer (9.84E+06).

Peptide ELISA-endpoint titer (sera collected after 3$^{rd}$ VLP administration.

| VLP | Animal # | 5.00E+02 1 | 1.50E+03 2 | 4.50E+03 3 | 1.35E+04 4 | 4.05E+04 5 | 1.22E+05 6 |
|---|---|---|---|---|---|---|---|
| AX09-0M3 | Bn. 1 | 4.360 | 4.305 | 4.278 | 4.246 | 4.163 | 3.489 |
| AX09-0M3 | Bn. 3 | 4.338 | 4.385 | 4.345 | 4.278 | 4.131 | 2.028 |
| AX09-0M3 | Bn. 5 | 4.332 | 4.359 | 4.291 | 4.276 | 4.204 | 3.371 |
| PBS | Pooled | 0.226 | 0.114 | 0.083 | 0.073 | 0.061 | 0.057 |

| VLP | Animal # | 3.65E+05 7 | 1.09E+06 8 | 3.28E+06 9 | 9.84E+06 10 | 2.95E+07 11 | 8.86E+07 12 |
|---|---|---|---|---|---|---|---|
| AX09-0M3 | Bn. 1 | 1.370 | 0.506 | 0.199 | 0.096 | 0.061 | 0.052 |
| AX09-0M3 | Bn. 3 | 0.749 | 0.297 | 0.130 | 0.078 | 0.064 | 0.051 |
| AX09-0M3 | Bn. 5 | 1.343 | 0.504 | 0.204 | 0.101 | 0.064 | 0.054 |
| PBS | Pooled | 0.058 | 0.060 | 0.054 | 0.050 | 0.048 | 0.049 |

| VLP | Animal | EPT |
|---|---|---|
| AX09-0M3 | Bn. 1 | 3.28E+06 |
| AX09-0M3 | Bn. 3 | 3.28E+06 |
| AX09-0M3 | Bn. 5 | 9.84E+06 |

Based on these results, mouse number B5 was selected to generate the monoclonal antibody.

For the generation of the monoclonal antibodies, splenocytes were mixed with NS-1 myeloma cells in a ratio 3:1 in DMEM medium supplemented with 10% FCS serum and a HAT solution (Ipoxantine 100 µM, Timidine 16 µM and Aminopterine 0.04 µM). 100 µl containing a total of 150,000 cells were plated in each well of fifteen 96-well-microtiter plates. After 10 days, an ELISA test was performed on supernatants from the wells in which cell growth was evident. 96 well plates were coated with antigen (100 µl of a 1 µg/mL xCT murine (m)ECD3 peptide solution) and incubated overnight at 4° C. Plates were washed 3 times with PBS and saturated with 200 µL BSA 3% in PBS for 1 hour at RT. Wells were washed 3 times with PBS and 70 µL of supernatant were added to each well and incubated for 1 hour at RT. After 5 washes with PBS, 50 µL of a 1:4000 dilution of Anti-Mouse IgG (whole molecule)-Peroxidase antibody produced in goat (SIGMA) were added in each well and incubated at RT for 1 hour. After washing the wells 5 times with PBS, 70 µL of TMB (tetrametylbenzidine, Sigma T0440) revealing solution were added to each well. The mix developed a yellow color and its intensity was evaluated by reading the 96 well plates at OD450 nm using a Gliomax Multi Plus detection system (Promega). Positive clones were selected, grown and again screened in ELISA. After three rounds of ELISA screening, 21 positive clones were identified and frozen.

FACS analysis of hybridoma clone supernatants form Bn.5 vaccinated mouse

| CLONE | I Elisa | II Elisa | III Elisa |
|---|---|---|---|
| 1D12 | 0.46 | 0.87 | 0.4 |
| 2A11 | 0.92 | 1.32 | 0.55 |
| 2D10 | 0.48 | 0.46 | 0.55 |
| 3E7 | 0.42 | 0.59 | 0.43 |
| 3E10 | 0.62 | 0.43 | 0.38 |
| 3F11 | 0.63 | 1.03 | 0.75 |
| 5B10 | 0.6 | 1.01 | 1.03 |
| 5E2 | 0.52 | 1.09 | 1.35 |
| 6B8 | 0.97 | 0.89 | 0.64 |
| 7A7 | 0.67 | 0.65 | 0.68 |
| 8F2 | 0.78 | 1.04 | 0.62 |
| 7H6 | 1.03 | 1.28 | 0.7 |
| 9C11 | 0.92 | 1.3 | 0.87 |
| 9E9 | 0.49 | 0.55 | 0.65 |

-continued

| CLONE | I Elisa | II Elisa | III Elisa |
|---|---|---|---|
| 10B9 | 0.42 | 0.73 | 0.86 |
| 11D1 | 0.55 | 0.54 | 0.96 |
| 11C6 | 0.78 | 1.39 | 0.78 |
| 12G9 | 0.44 | 1.2 | 0.63 |
| 13G8 | 0.98 | 1.25 | 0.56 |
| 14C2 | 0.56 | 1.53 | 1.6 |
| 15F5 | 0.53 | 1.14 | 1.2 |

The 21 hybridoma clones were tested by immunoflourecence (IF) on 4T1 (4T1-P1) and HCC1806 (HCC1806-P1) derived tumorspheres. For IF assay 2×10$^5$ tumorspheres/sample were cytospun to a glass slide, fixed in 4% formaldehyde and then incubated with 100 µl of undiluted hybridoma clones' culture supernatant for 1 hour at room temperature. Then, goat anti-mouse Ig (H+L) AlexaFluor-488 was used as secondary antibody (Life Technologies). The rabbit anti-xCT antibody (PA1-16775; Thermo Fisher) was used as positive control using citospun fixed tumorspheres previously permeabilized with 0.2% Triton X-100. Then, goat anti-rabbit AlexaFluor-538 was used as secondary antibody (Life Technologies). Images were acquired on ApoTome system and AxioVision Release 4.8 software (Zeiss). The samples, which resulted positive in IF on both 4T1-P1 and HCC1806-P1, i.e. clones 5E2, 8F2, 7H6, 11D1, 11C6, and 14C2, were thawed and tested again by ELISA.

Based on ELISA and IF analysis, the 11D1 clone was selected and subcloned by plating 1 cell per well in three, 96-well-microtiter plates. 61 clones were obtained, and 5 clones were positive in ELISA against the mECD3 peptide, namely: 11D1/C3; 11D1/H7; 11D1/E7; 11D1/E5; 11D1/H10. Following another ELISA assays performed by using the human-xCT protein (FIG. 8) and new IF analysis by using HCC1806-P1, three subclones were selected: H10, C3, and E7 and tested by ELISA against the human-xCT ECD3 peptide [1 μg/mL] (FIG. 9). From this ELISA H10 (from here called 11D1/H10) was chosen as the subclone having the better ability to produce anti-xCT Ig. In order to discriminate which Ig isotype was present into the supernatants from 11D1/H10, a Pierce rapid isotyping kit was used (#26178; Thermo Scientific) (FIG. 10).

11D1/H10 clone hybridoma cells were grown in a Bioreactor (CELLINE 1000 WHEATON) to obtain a high Ab titer. Each week, for 4 weeks, 10 mL of concentrated supernatant were taken and tested by FACS for their ability to stain 4T1 P2 tumorspheres. Then, Ig was purified from 3 mL of 11D1/H10 supernatant on protein A-sepharose. 1.5 mL of purified monoclonal Ab were obtained at a concentration of 0.7 mg/mL and tested by using the Pierce rapid ELISA mouse mAb Isotyping kit (#37503; Invitrogen) and the Pierce rapid isotyping kit (#26178; ThermoScientific), in order to identify the Ig isotypes (FIG. 11). These data suggest that the 11D1/H10 is not a clone, but contains cells producing different Ig isotypes. For this reason, 11D1/H10 was subcloned, obtaining 30 new clones, then tested by ELISA. Five of these clones resulted secreting Ig (ELISA O.D. 450≥0.400) against xCT. The culture supernatants from these subclones (A1, A5, B9, D5, adn E1) were tested for the presence of anti-xCT Ig or Ig isotypes (FIG. 12-16). At this step, Ig isotypes were tested by using three different methods: ELISA (as previously described, using human-xCT ECD3); the Pierce rapid ELISA mouse mAb Isotyping kit (#37503; Invitrogen); the Pierce rapid isotyping kit (#26178; ThermoScientific). This analysis identified the presence of specific anti-xCT antibodies belonging to the IgM (-kappa) isotype, for each subclones tested. These subclones were sent for Antibody Full Length Sequencing. The sequence for all five clones was identical, and a representative sequence includes:

The heavy chain DNA sequence for antibody H1E1 is in SEQ ID NO:13. SEQ ID NO:13 encodes Heavy chain: Amino acids sequence (595 aa) SEQ ID NO:14 having a CDR1 with amino acids of SEQ ID NO:15; CDR2 having the amino acids of SEQ ID NO:16; and CDR3 having the amino acids or SEQ ID NO:17.

The light chain: DNA sequence (708 bp) for antibody H1E1 is in SEQ ID NO:18) that encodes Light chain: Amino acids sequence (235 aa) of SEQ ID NO:19 having CDR1 having the amino acid sequence of SEQ ID NO:20, CDR2 having an amino acid sequence of SEQ ID NO:21, and CDR3 having an amino acid sequence of SEQ ID NO:22.

Materials—

H1E1 Hybridoma cell; TRIzol® Reagent (Ambion, Cat. No.: 15596-026); PrimeScript™ 1st Strand cDNA Synthesis Kit (Takara, Cat. No.: 6110A).

Methods—

Total RNA was isolated from the hybridoma cells following the technical manual of TRIzol® Reagent. Total RNA was then reverse-transcribed into cDNA using either isotype-specific anti-sense primers or universal primers following the technical manual of PrimeScript™ 1st Strand cDNA Synthesis Kit. Antibody fragments of VH, VL, CH and CL were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned and the consensus sequence was provided.

The invention claimed is:

1. An xCT antibody comprising a heavy chain comprising a CDR1 having the amino acid sequence of SEQ ID NO:15, a CDR2 having the amino acid sequence of SEQ ID NO:16, and a CDR3 having the amino acid sequence of SEQ ID NO:17; and a light chain comprising a CDR1 having the amino acid sequence of SEQ ID NO:20, a CDR2 having the amino acid sequence of SEQ ID NO:21, and a CDR3 having the amino acid sequence of SEQ ID NO:22.

2. The xCT antibody of claim 1, wherein the antibody is humanized.

3. The xCT antibody of claim 1, wherein the antibody is chimeric.

4. The antibody of claim 1, wherein the antibody is an antibody fragment.

5. The antibody of claim 4, wherein the antibody fragment is an ScFv.

6. The antibody of claim 5, wherein the ScFv is murine or humanized.

7. A method of treating a patient having pancreatic cancer, gastrointestinal cancer, lung cancer, breast cancer, cervical cancer, uterine cancer, ovarian cancers, colorectal cancer, or stomach cancer, comprising administering an effective amount of the anti-xCT antibody of claim 1, or the antibody fragment of claim 4 to the patient.

8. The method of claim 7, wherein the anti-xCT antibody or the antibody fragment is humanized.

9. The method of claim 7, wherein the anti-xCT antibody or the antibody fragment is chimeric.

10. The method of claim 7, wherein the antibody fragment is an ScFv.

11. The method of claim 10, wherein the ScFv is murine or humanized.

12. The method of claim 7, wherein the patient is a human or a non-human animal.

13. The method of claim 7, wherein the anti-xCT antibody or the antibody fragment is administered parenterally, intraperitoneally, intravenously, subcutaneously, orally, nasally, via inhalation, or rectally.

14. The method of claim 7, wherein the anti-xCT antibody or the antibody fragment is administered intravenously at a dosage of from 5 $mg/m^2$ to 2000 $mg/m^2$.

* * * * *